(12) United States Patent
Anzai et al.

(10) Patent No.: US 9,533,070 B2
(45) Date of Patent: Jan. 3, 2017

(54) THERAPEUTIC AGENT FOR PULMONARY EMPHYSEMA

(75) Inventors: Takao Anzai, Kanagawa (JP); Atsuhiko Nogawa, Kanagawa (JP); Yuichi Tada, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/818,419

(22) PCT Filed: Aug. 10, 2011

(86) PCT No.: PCT/JP2011/068318
§ 371 (c)(1),
(2), (4) Date: Mar. 20, 2013

(87) PCT Pub. No.: WO2012/026336
PCT Pub. Date: Mar. 1, 2012

(65) Prior Publication Data
US 2013/0178426 A1   Jul. 11, 2013

Related U.S. Application Data

(60) Provisional application No. 61/376,825, filed on Aug. 25, 2010.

(30) Foreign Application Priority Data

Sep. 29, 2010   (JP) .................................. 2010-219330

(51) Int. Cl.
| | |
|---|---|
| A61L 24/10 | (2006.01) |
| A61L 24/06 | (2006.01) |
| A61L 24/08 | (2006.01) |
| A61M 16/04 | (2006.01) |
| A61K 9/00 | (2006.01) |
| A61L 31/04 | (2006.01) |
| A61L 31/14 | (2006.01) |
| A61B 17/12 | (2006.01) |
| A61M 25/10 | (2013.01) |

(52) U.S. Cl.
CPC ........ *A61L 24/104* (2013.01); *A61B 17/12181* (2013.01); *A61K 9/007* (2013.01); *A61L 24/06* (2013.01); *A61L 24/08* (2013.01); *A61L 31/042* (2013.01); *A61L 31/145* (2013.01); *A61M 16/04* (2013.01); *A61M 16/0404* (2014.02); *A61B 17/12045* (2013.01); *A61L 2430/36* (2013.01); *A61M 2025/1052* (2013.01); *A61M 2202/0007* (2013.01); *A61M 2202/0208* (2013.01); *A61M 2202/0225* (2013.01); *A61M 2202/0488* (2013.01); *A61M 2202/064* (2013.01); *A61M 2210/1039* (2013.01)

(58) Field of Classification Search
CPC ........ A61M 16/04; A61K 9/007; A61L 24/06; A61L 24/08; A61L 24/104
See application file for complete search history.

(56) References Cited

U.S. PATENT DOCUMENTS

| | | |
|---|---|---|
| 5,575,815 A | 11/1996 | Slepian et al. |
| 6,258,100 B1 | 7/2001 | Alferness et al. |
| 6,287,290 B1 | 9/2001 | Perkins et al. |
| 6,610,043 B1 | 8/2003 | Ingenito |
| 6,682,520 B2 | 1/2004 | Ingenito |
| 6,878,141 B1 * | 4/2005 | Perkins et al. ................ 604/516 |
| 7,300,428 B2 | 11/2007 | Ingenito |
| 7,468,350 B2 | 12/2008 | Gong et al. |
| 7,549,984 B2 | 6/2009 | Mathis |
| 7,553,810 B2 | 6/2009 | Gong et al. |
| 7,608,579 B2 | 10/2009 | Gong et al. |
| 7,654,998 B1 | 2/2010 | Ingenito |
| 7,654,999 B2 | 2/2010 | Ingenito |
| 7,678,767 B2 | 3/2010 | Gong et al. |
| 7,932,225 B2 | 4/2011 | Gong et al. |

(Continued)

FOREIGN PATENT DOCUMENTS

| | | |
|---|---|---|
| JP | 09-506011 A | 6/1997 |
| JP | 2003-503162 | 1/2003 |

(Continued)

OTHER PUBLICATIONS

Written Opinion (PCT/ISA/237) issued Nov. 15, 2011 by the Japanese Patent Office as the International Searching Authority for International Application No. PCT/JP/2011/068318 and English language translation of the Written Opinion, and Notification of Transmittal of Translation of International Preliminary Report on Patentability (9 pages).

(Continued)

*Primary Examiner* — Satyanarayana R Gudibande
*Assistant Examiner* — Jia-Hai Lee
(74) *Attorney, Agent, or Firm* — Buchanan Ingersoll & Rooney PC

(57) ABSTRACT

The invention has as its object the provision of a medicine capable of reducing a volume of emphysema-suffering pulmonary alveoli or alveolar sacs by means of a respiratory region volume inhibitor containing a coating film formation as a main component and capable of forming a coating film in a respiratory region, characterized by being used in such a way that the coating film-forming component is administered to an emphysema-suffering pulmonary alveolar parenchyma in a human-respiratory region in an amount of 0.004 to 200 g/application, preferably 0.07 to 20 g/application and more preferably 0.5 to 5 g/application on each occasion.

10 Claims, 13 Drawing Sheets

(56) References Cited

U.S. PATENT DOCUMENTS

| | | | |
|---|---|---|---|
| 2002/0064558 A1* | 5/2002 | Tanaka | A61L 33/064 424/486 |
| 2003/0181356 A1 | 9/2003 | Ingenito | |
| 2005/0281797 A1 | 12/2005 | Gong | |
| 2006/0264772 A1 | 11/2006 | Aljuri et al. | |
| 2007/0110813 A1 | 5/2007 | Ingenito et al. | |
| 2008/0097139 A1 | 4/2008 | Clerc | |
| 2008/0261884 A1 | 10/2008 | Tsai et al. | |
| 2008/0281352 A1 | 11/2008 | Ingenito et al. | |
| 2009/0012626 A1 | 1/2009 | Thompson et al. | |
| 2009/0076623 A1 | 3/2009 | Mathis et al. | |
| 2009/0104183 A1 | 4/2009 | Gong et al. | |
| 2009/0181096 A1* | 7/2009 | Ludwig | 424/489 |
| 2010/0070050 A1 | 3/2010 | Mathis et al. | |
| 2010/0297218 A1 | 11/2010 | Gong et al. | |
| 2010/0305715 A1 | 12/2010 | Mathis et al. | |
| 2012/0053513 A1 | 3/2012 | Tada et al. | |

FOREIGN PATENT DOCUMENTS

| | | |
|---|---|---|
| JP | 2003507130 A | 2/2003 |
| JP | 2003518190 A | 6/2003 |
| JP | 2009504342 A | 2/2009 |
| JP | 2009-514860 | 4/2009 |
| JP | 2009514860 A | 4/2009 |
| JP | 2010526914 A | 8/2010 |
| WO | 01/13908 A2 | 3/2001 |
| WO | 01/46327 A2 | 6/2001 |
| WO | 2007/022377 A2 | 2/2007 |
| WO | 2007/055950 A2 | 5/2007 |
| WO | WO 2007055950 A2 * | 5/2007 |
| WO | 2008/141059 A2 | 11/2008 |
| WO | WO 2009/075106 A1 | 6/2009 |

OTHER PUBLICATIONS

International Search Report (PCT/ISA/210) issued on Nov. 15, 2011, by the Japanese Patent Office as the International Searching Authority for International Application No, PCT/JP2011/068318.

Written Opinion (PCT/ISA/237) issued on Nov. 4, 2011, by the Japanese Patent Office as the International Searching Authority for International Application No. PCT/JP2011/068318.

Jadranka Spahiga et al., "Effects of Imposed Pursed-Lips Breathing on Respiratory Mechanics and Dyspnea at Rest and During Exercise in COPD," Chest, Aug. 2005; 128; pp. 640-650.

Jan A. Van Noord et al., "Effects of Tiotropium With and Without Formoterol on Airflow Obstruction and Resting Hyperinflation in Patients with COPD," Chest, Mar. 2006; 129; pp. 509-517.

Ware JH et al., "Cost Effectiveness of Lung-Volume-Reduction Surgery for Patients with Severe Emphysema," The New England Journal of Medicine, 348;21, May 2003, pp. 2092-2102.

National Emphysema Treatment Trial Research Group, "A Randomized Trial comparing Lung-Volume-Reduction Surgery with Medical Therapy for Severe Emphysema," New England Journal of Medicine, 348;21, May 2003, pp. 2059-2073.

Edward P. Ingenito, "Bronchoscopic Lung Volume Reduction Using Tissue Engineering Principles," Am. J. Respir, Crit, Card Med., 2003 (month unknown), vol. 167, pp. 771-778.

Koichi Kaneko, "Current State and Prospect of Fibrin Adhesive in Lung Surgery, Spontaneous Pneumothorax and Pulmonary Emphysema," Surgery Frontier, Sep. 1, 2001, vol. 8 No. 3, pp. 336-340 (with English translation).

Yoichi Watanabe et al., "Endoscopic Lung Volume Reduction for Severe Pulmonary Emphysema using EWS," The Journal of the Japanese Respiratory Society, Jun. 10, 2006, vol. 44, pp. 290 (with English translation).

First Office Action issued in U.S. Appl. No. 13/216,912, dated Sep. 4, 2014.

Office Action issued in China Appln. No. 2011841265.0, dated Mar. 4, 2014, with English translation (10 pages).

Kobayashi H. and Kanoh S., "Bronchoscopic Autologous Blood Injection for Lung Volume Reduction", Journal of Japanese Respiratory Society, 2009, vol. 47, No. 9, pp. 765-771.

Reilly J. et al., "Biological Lung Volume Reduction", Chest, 2007 vol. 131, No. 4, pp. 1108-1113.

An Official Reason for Rejection issued in corresponding Japan Appl. No. 2010-219330, dated Sep. 2, 2014.

Supplementary European Search Report in EP App. No. 11 81 9800 dated Jan. 11, 2016.

* cited by examiner

THERAPEUTIC AGENT FOR PULMONARY EMPHYSEMA

TECHNICAL FIELD

This invention relates to a method for treating pulmonary emphysema. More particularly, the invention relates to a method for treating pulmonary emphysema by reducing the volume of pulmonary alveoli or alveolar sacs wherein an abnormal enlargement is developed in association with destruction with pulmonary emphysema.

BACKGROUND ART

Chronic obstructive pulmonary disease (COPD) means a wide variety of groups of lung diseases impeding normal breathing and is a disease of lung obstruction by the presence of at least one disease selected from asthma, pulmonary emphysema and chronic bronchitis. COPD is such that these diseases frequently co-exist at the same time and a difficulty is involved in confirming whichever disease is a cause bringing about lung obstruction in individual diseases. In clinical aspect, COPD has been diagnosed by a lowering of an expiratory flow rate from the lungs, which is kept constant over several months and which continuously continues over two years in cases of chronic bronchitis. The two most serious states related with COPD include chronic bronchitis and pulmonary emphysema.

Of these, pulmonary emphysema means a state where an abnormal enlargement develops bringing about the destruction of tissues called pulmonary alveolar parenchyma such as of alveolar bronchioles, pulmonary alveoli, alveolar sacs or the like serving as a gas exchange site. Although the pulmonary alveolar parenchyma in its normal state shrinks during expiration, emphysema-suffering pulmonary alveolar parenchyma does not return to its original state if once enlarged by breathing. Therefore, one cannot breathe well. Besides, the effective area and vascular bed (blood capillaries running randomly throughout the surfaces of the pulmonary alveoli) of the pulmonary alveoli decrease, thereby lowering the ventilatory function of the lungs as a whole. Additionally, since elastin, collagen and the like are destroyed from inflammation, the elasticity of lung lowers and it is not thus possible to expand the lung by pulling the respiratory tract open, so that the bronchi are in a condition of likelihood of deformation. Accordingly, as set out in PCT International Publication No. WO2009/075106 Pamphlet, when the lungs contract upon breathing, the bronchi thereof is narrowed by being compressed with the pulmonary alveoli filled with air, with the result that the lungs are hyperinflated, thus making it difficult to release the air. To cope with this, as set out, for example, in [Jadranka Spahija et al., "Effects of Imposed Pursed-Lips Breathing on Respiratory Mechanics and Dyspnea at Rest and During Exercise in COPD," Chest 2005; 128:640-650], patients with pulmonary emphysema exhale through pursed-lips breathing so as to breathe out air.

In Japan, about 50,000 persons suffer this disease and have now undergone home oxygen therapy. It is said that when including those persons having a mild disease condition, about three million persons are regarded as backup candidates for pulmonary emphysema. For the therapy, the home oxygen therapy is main treatment at present. The oxygen therapy has been frequently used in a condition where sufficient oxygen cannot be absorbed from air because pulmonary function is severely impaired. However, this therapy merely alleviates symptoms and is thus not an effective treatment. For drug therapy, for example, mention is made of: a method wherein a bronchodilator is used to help keep the airways in the lungs open thereby alleviating the shortness of breath as described in [Jan A. van Noord et al., "Effects of Tiotropium With and Without Formoterol on Airflow Obstruction and Resting Hyperinflation in Patients with COPD," Chest 2006; 129: 509-517]; a method of reducing inflammation in the airways by use of an inhaled steroid drug or peroral steroid drug; a method of preventing and treating additional inflammation by use of antibiotics; and a method of eliminating the mucus from the airways by using an expectorator.

However, as described in [Ware J H, et al., "Cost effectiveness of Lung-Volume-Reduction Surgery for Patients with Sever Emphysema," The new England Journal of Medicine 2003; 348:2005-2056] and also in [National Emphysema Treatment Trial Research Group, "A Randomized Trial Comparing Lung-Volume-Reduction Surgery with Medical Therapy for Severe Emphysema," The new England Journal of Medicine 2003; 348:2059-2073], all these drug therapies help control the pulmonary emphysema and alleviate the symptoms, but are not an effective treatment. In addition, there are known a surgical therapy such as a lung reduction operation wherein the damaged portion of lung is removed to allow a normal part of lung to be enlarged, and lung transplantation. However, these methods would impose a great burden on patients and it is difficult to secure a lung substitute.

If lung volume reduction (LVR) can be non-invasively achieved without thoracotomy, there can be given a chance for treatment of more patients. Nevertheless, the success rate of the existing non-invasive treatment is low. For the non-invasive treatment, there is known an apparatus of impeding an inspiration inflow toward the terminal direction of lung by indwelling a structure having a unidirectional valve mechanism inside the bronchus so as to obtain similar effects to the lung volume reduction surgery (LVRS) as set forth, for example, in the U.S. Pat. No. 6,258,100 specification. However, in case where these structures have been indwelled, there is pointed out, in the U.S. Pat. No. 7,549,984, a problem in that easy access to ahead of the structures becomes difficult.

It is known that in the destroyed alveolar bronchiole or pulmonary alveolar parenchyma, there exists an air flow path called collateral channel and different from the main airway. Accordingly, as described in the Publication of United States Patent Application No. 2006/0264772, the air flow passing through the main airway can be impeded by means of the structure. Nevertheless, where collateral channels exist, air arrives at the inside of the destroyed alveolar bronchiole or pulmonary alveolar parenchyma while taking a detour path around the block with the structure, so that the lung enlargement cannot be prevented.

For a measure of achieving non-surgical lung volume reduction, there is disclosed, in Patent Document 5, a method of realizing LVR wherein a region of lung is collapsed and part of the collapsed region is bonded to other region to promote desmoplasia in the bonded tissues or therearound. In this method, however, the collapse of the pulmonary alveolar parenchyma by vital reaction has to be waited. Moreover, in the U.S. Pat. No. 6,682,520 specification, a trial method of LVR is described using a material containing a site of targeting damaged lung tissues. However, the U.S. Pat. No. 7,678,767 indicates that this method not only needs the targeting site, but also needs a process of reaction with the damaged site. Hence, an effective treating method of pulmonary emphysema is not now known in this field.

The disease state where pulmonary emphysema is an underlying disease like COPD includes pneumothorax. The pneumothorax is a disease state where a hole is made in the visceral pleura surrounding the lung per se and air is leaked into a space inside the lung inbetween with the visceral pleura at the side of thorax.

Where breathing is prevented by pneumothorax, there is performed a drainage method wherein a tube is inserted through an incision in the chest wall and the air inbetween the parietal pleura and the visceral pleura is drained, or a resection treatment of cystectomy under thoracoscopy. However, with the drainage method, it takes several or more days for healing and the treatment under thoracoscopy is a sort of operation, with high invasiveness on the part of patient. The pneumothorax is high in rate of recurrence and thus, there have been demanded a shortage in time required for one treatment and a reduction in operation invasiveness.

DISCLOSURE OF INVENTION

As stated above, although mention is made, as the COPD treatment, of a domiciliary oxygen therapy, a drug therapy, a respiratory rehabilitation program, a non-invasive positive airway pressure therapy making use of a nasal mask, and a lung volume reduction surgery therapy. However, none of these therapies are useful, and these therapies involve a difficulty in selectively blocking only a respiratory region containing a major proportion of emphysema-suffering pulmonary alveolar parenchyma, with the result that the inflow of air into a normal respiratory region is impeded thereby lowering a normal ventilator function of lung. Moreover, where an emphysema portion is damaged, air will be flown into between the parietal pleura and the visceral pleura.

Accordingly, the invention primarily has as its object the provision of a medicine capable of reducing a volume of emphysema-suffering pulmonary alveoli or alveolar sacs by means of a respiratory region volume inhibitor containing a coating film-forming component as a main component and capable of forming a coating film in a respiratory region, characterized by being used in such a way that the coating film-forming component is administered to an emphysema-suffering pulmonary alveolar parenchyma in a human-respiratory region in an amount of 0.004 to 200 g/application, preferably 0.07 to 20 g/application and more preferably 0.5 to 5 g/application on each occasion.

DETAILED DESCRIPTION

Figure 1A:
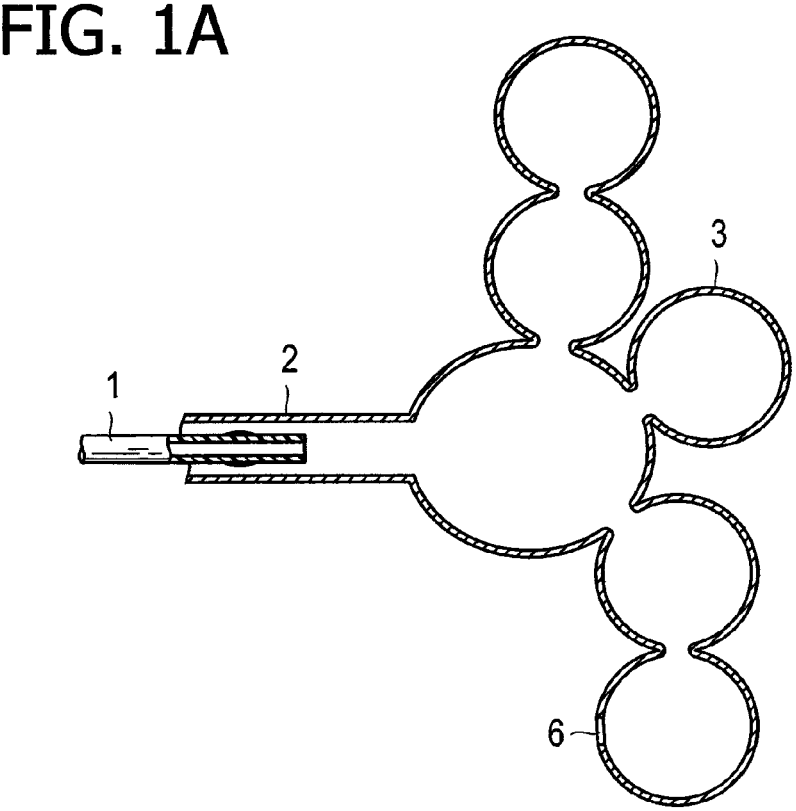
FIG. 1A is a schematic sectional view showing a step in sequence of a method of the invention.

A primary aspect of the invention resides in a respiratory region volume inhibitor containing a coating film-forming component as a main component and capable of forming a coating film in a respiratory region, characterized by being used in such a way that the coating film-forming component is administered to an emphysema-suffering pulmonary alveolar parenchyma in a human-respiratory region in an amount of 0.004 to 200 g/application, preferably 0.07 to 20 g/application and more preferably 0.5 to 5 g/application on each occasion.

According to the invention, in order to efficiently remove air retained in the emphysema-suffering pulmonary alveoli or alveolar sacs (which may be hereinafter referred to simply as "pulmonary alveolar parenchyma") or to maintain the volume thus reduced by breathing, lung hyperinflation, which is one of factors of debilitating an affected individual by obstruction in pulmonary emphysema and air-passage bronchi, can be alleviated or suppressed. Moreover, when the size of the emphysema-suffering pulmonary alveolar parenchyma is made smaller than the original one, the compression of or obstruction in neighboring bronchi with the pulmonary alveolar parenchyma located therearound can be suppressed or prevented. The treating method of the invention is one making use of a catheter and does not need any surgical procedure, and can thus reduce a burden on patient.

With normal lungs, it is usual that there are no collateral channels existing between both lungs or only a very small number of the channels if existing. However, it is often the case that the emphysema-suffering pulmonary alveolar parenchyma has pores, which are called collateral channels connecting with neighboring pulmonary alveoli. Hence, if a catheter is inserted into the pulmonary alveolar parenchyma in a hyperinflated state ascribed to the development of emphysema so as to suction air therefrom, air flows in from the collateral channels, so that the lung hyperinflation cannot be alleviated. In contrast thereto, in the practice of the invention, a respiratory region volume inhibitor is injected into a respiratory region including pulmonary alveoli or alveolar sacs to form a coating film on an inner wall of the respiratory region, thereby enabling the emphysema-suffering pulmonary alveolar parenchyma to be formed substantially as a closed system. Accordingly, even if collateral channels exist in the emphysema-suffering pulmonary alveolar parenchyma, little or no air leaks out upon removal by suction of air from the emphysema-suffering pulmonary alveolar parenchyma. Thus, the air in the closed system can be reliably removed and the volume of the pulmonary alveolar parenchyma can be readily, efficiently and rapidly reduced.

Although the single amount (dose) of the coating film-forming component according to the invention depends on the age of patient, the severity of symptoms and the like, it is preferred to use 0.004 to 200 g/application, preferably 0.07 to 20 g/application and more preferably 0.5 to 5 g/application of the coating film-forming component.

The respiratory region volume inhibitor of the invention is preferably made of a composition including a coating film-forming component as a main component, a coating film adjusting component and a solvent. It is preferred to use the coating film adjusting component at 0.1 to 100 parts by mass and the solvent at 100 to 5000 parts by mass, more preferably the coating film adjusting component at 1 to 50 parts by mass and the solvent at 500 to 3000 parts by mass, and much more preferably the coating film adjusting component at 5 to 25 parts by mass and the solvent at 1000 to 2000 parts by mass, per 100 parts by mass of the coating film-forming component.

The use of the coating film adjusting component within a range of 1 to 50 parts by mass per 100 parts by mass of the coating film-forming component is preferred from a standpoint that adequate film strength can be developed while keeping an injectable viscosity.

The use of the solvent within a range of 1000 to 2000 parts by mass per 100 parts by mass of the coating film-forming component is preferred from the standpoint that adequate film strength can be developed while keeping an injectable viscosity.

It will be noted that "dose" used herein means an initial dose which is first administered to patient in one operation and with a case of recovery after the administration, a recovered amount is not included.

The respiratory region volume inhibitor according to the invention is one using the coating film-forming component as the main component. Preferably, the coating film-forming component is so configured that a balloon-shaped closed pouch made of the coating film is formed in intimate contact with the inner surface of the respiratory region along an inner peripheral surface of the respiratory region in response to an external stimulation and is shrunk by reducing a pressure in the balloon-shaped closed pouch from outside of the respiratory region.

This allows the coating film in the form of a balloon-shaped closed pouch to be formed in intimate contact with inner walls of the emphysema-suffering pulmonary alveolar parenchyma, so that the elasticity of the emphysema-suffering pulmonary alveolar parenchyma is restored and thus, lung hyperinflation can be alleviated and suppressed.

More particularly, with a case where a stimulation responsive material capable of forming a film in response, for example, to moisture, divalent metal ions, oxygen, hydrogen, nitrogen, a polymer electrolyte or the like for use as an external stimulation is employed as the coating film-forming component according to the invention, when a respiratory region volume inhibitor made mainly of the coating film-forming component is injected into and around the emphysema-suffering pulmonary alveolar parenchyma, an external stimulation, such as moisture or calcium, on the surface of the inner walls of the respiratory region and the coating film-forming component react with each other to form a coating film by coverage of and in intimate contact with the full surface of the inner walls of the respiratory region. In addition, the coating film becomes a closed system except for an injection port for the respiratory region volume inhibitor and thus the balloon-shaped closed pouch constituted of the coating film is formed in intimate contact with the inner walls of the pulmonary alveolar parenchyma. Moreover, the coating film in the form of the balloon-shaped closed pouch is cured depending on the amount of the external stimulation, the time and the like, so that the balloon-shaped closed pouch undergoes shrinkage without breakage when reduced in inside pressure thereof. Therefore, the air inside the balloon-shaped closed pouch can be reliably removed and the volume of the pulmonary alveolar parenchyma can be reduced readily, efficiently and rapidly. The coating film of the balloon-shaped closed pouch is solidified with a lapse of time, or the curing rate of the coating film is low and the film formation is completed after shrinkage, so that the shrunk state of the emphysema-suffering pulmonary alveolar parenchyma can be held. In this way, the volume of the pulmonary alveolar parenchyma can be efficiently reduced and the volume reduced by breathing can be maintained. Thus, it is considered that the lung hyperinflation, which is one of factors of debilitating an affected individual by blockage in pulmonary emphysemas and air-passage bronchi, can be alleviated and suppressed.

Preferably, the balloon-shaped closed pouch according to the invention is formed in intimate contact with the inner surface of the respiratory region along the inner peripheral surface of the respiratory region (e.g. pulmonary alveolar parenchyma), after which the balloon-shaped closed pouch is reduced in inside pressure from outside of the respiratory region to permit the balloon-shaped closed pouch and the respiratory region to be integrally shrunk. This can suppress or prevent the neighboring bronchi from being compressed or blocked with the surrounding normal pulmonary alveolar parenchyma.

The external stimulation according to the invention means a chemical substance or physical factor responsive to the coating film-forming component and is a sort of concept including the coating film-forming component per se. The external stimulation per se may be either an in-vivo-derived component or a component separately contained in the respiratory region volume inhibitor of the invention. The external stimulation of the invention should preferably contain an external stimulation component. As such a component, mention is made of moisture, divalent metal ions, a reactant gas such as oxygen, hydrogen or nitrogen, a polymer electrolyte or the like.

The coating film-forming component according to the invention is preferably one that is able to form a balloon-shaped closed pouch constituted of the coating film in response to an external stimulation. The coating film-forming component is preferably made of a material that allows easy bonding between the balloon-shaped closed pouch and the respiratory region (e.g. the pulmonary alveolar parenchyma). In doing so, the balloon-shaped closed film pouch is formed, for example, in intimate contact with the inner surface of the respiratory region along the inner peripheral surface of the pulmonary alveolar parenchyma, after which the pulmonary alveolar parenchyma and the balloon-shaped closed pouch can be integrally shrunk. The materials for the coating film-forming component preferably include polymers or film-forming polymer precursors (monomers). More preferably, there are mentioned tacky polymers, film-forming polymer precursors or polymer electrolytes.

A tacky polymer means a high-molecular-weight polymer exhibiting tackiness (adhesiveness) when applied to body tissues such as pulmonary alveolar parenchyma. No specific limitation is placed on the type of tacky polymer in so far as the polymer has adhesiveness to the pulmonary alveolar parenchyma and is capable of blocking collateral channels, and materials ordinarily employed in the medical field may be likewise used. In particular, mention is made of starch, gum arabic, sodium alginate, propylene glycol alginate, carboxyvinyl polymer, carmellose sodium, xanthan gum, gellan gum, gelatin, hydrolyzed gelatin, polyacrylic acid, polyacrylate, partially neutralized polyacrylic acid, starch polyacrylate, polyvinylpyrrolidone, hydroxyethyl cellulose, hydroxypropyl cellulose, hydroxypropylmethyl cellulose, polyvinyl alcohol (PVA), methylcellulose (MC), carboxymethyl cellulose (CMC), sodium carboxymethyl cellulose and the like. The tacky polymers may be used singly or in admixture of two or more. Of these tacky polymers, water-soluble polymers are preferred including carboxyvinyl polymer, hydroxyethyl cellulose, hydroxypropyl cellulose, hydroxypropylmethyl cellulose, polyvinyl alcohol, methylcellulose, starch, sodium alginate, gelatin, hydrolyzed gelatin and the like, among which starch, sodium alginate, gelatin and hydrolyzed gelatin are more preferred. These are excellent in tackiness (adhesiveness) to body tissues and are unlikely to drip off from an applied site. Films made of these materials show excellent integrity with the inner walls of the emphysema-suffering pulmonary alveolar parenchyma, so that separation of the film is unlikely to occur or does not occur after reduction in size of the pulmonary alveolar parenchyma.

The concentration of the tacky polymer in the respiratory region volume inhibitor is not critical and is preferably at 0.5 to 50% by mass. Within such a concentration, the respiratory region volume inhibitor exhibits good tackiness (adhesiveness) to the inner walls of the pulmonary alveolar parenchyma.

The weight average molecular weight of the tacky polymer according to the invention is not critical and is preferably at 10000 to 10000000, more preferably at 100000 to 5000000 and much more preferably at 500000 to 2500000.

It will be noted that the measurement of the weight average molecular weight can be performed according to known methods and can be calculated, for example, from light scattering, a chromatographic method such as GPC, a viscosity measuring method, TOFMASS or the like. The weight average molecular weight used herein is determined by measurement with GPC (made by Waters Corporation).

The film-forming polymer precursor according to the invention is not critical in type so far as it is able to initiate reaction (curing) with moisture on the surface of body tissues such as of the pulmonary alveolar parenchyma, or is able to block the collateral channels if present. Specifically, cyanoacrylate monomers are preferably used. On this occasion, when contacting with moisture, cyanoacrylate monomers are polymerized into polycyanoacrylates. Specifically, mention is made of: alkyl and cycloalkyl α-cyanoacrylates such as methyl α-cyanoacrylate, ethyl α-cyanoacrylate, propyl α-cyanoacrylate, butyl α-cyanoacrylate, cyclohexyl α-cyanoacrylate, heptyl α-cyanoacrylate and octyl α-cyanoacrylate; alkenyl and cycloalkenyl α-cyanoacrylates such as allyl α-cyanoacrylate, methallyl α-cyanoacrylate and cyclohexenyl α-cyanoacrylate; alkynyl α-cyanoacrylates such as propangyl α-cyanoacrylate; aryl α-cyanoacrylates such as phenyl α-cyanoacrylate and toluoyl α-cyanoacrylate; hetero atom-containing methoxyethyl α-cyanoacrylate, ethoxyethyl α-cyanoacrylate and furfuryl α-cyanoacrylate; and silicon-containing trimethylsilylmethyl α-cyanoacrylate, trimethylsilylethyl α-cyanoacrylate, trimethylsilylpropyl α-cyanoacrylate and dimethylvinylsilylmethyl α-cyanoacrylate. These α-cyanoacrylates may be used singly or in admixture of two or more. Of these, cyclohexyl α-cyanoacrylate, heptyl α-cyanoacrylate, octyl α-cyanoacrylate, ethyl α-cyanoacrylate and the like are preferred. The cyanoacrylates having such a long ester side chain length as indicated above are soft when converted to a polymerized cured product thereof (a cured layer), thereby permitting the emphysema-suffering pulmonary alveolar parenchyma (alveoli or alveolar sacs) to be readily shrunk.

As a polymer electrolyte, mention is made of polymer electrolytes having a negative charge and polymer electrolytes having a positive charge.

The polymer electrolyte having a negative charge is not critical in type so far as it has at least one anionic group, preferably two or more anionic groups. For instance, mention is made of: polyamino acids; artificially synthesized polypeptides; polysaccharides such as heparin, hyaluronic acid, chondroitin, pectin, agarose, glycosaminoglycan, cellulose and starch; artificially synthesized polysaccharides and the like. These polymer electrolytes may be used singly or in admixture of two or more. Of these, heparin, hyaluronic acid, chondroitin, pectin, agarose and glycosaminoglycan are preferred, and heparin hyaluronic acid is more preferred.

The polymer electrolytes having a negative charge may be obtained by polymerizing monomers having a negative charge. As a monomer having a negative charge, mention is made of those monomers having at least one functional group selected from a sulfo group ($—SO_3H$), a carboxyl group ($—COOH$), a phosphonate group ($—PO_3H_2$) and the like although not limited thereto.

Although not limitative, monomers having a sulfo group ($—SO_3H$) include, for example, vinylsulfonic acid (ethylene sulfonic acid), 2-propene sulfonic acid, 3-butene sulfonic acid, 4-pentene sulfonic acid, sulfomethyl (meth)acrylate, 2-sulfoethyl (meth)acrylate, 3-sulfopropyl (meth)acrylate, 2-methyl-3-sulfopropyl (meth)acrylate, 4-sulfobutyl (meth)acrylate, 4-sulfobutyl N-(2-sulfoethyl)(meth)acrylate, 2-(meth)acrylamido-2-methylpropane sulfonic acid, N-(2-sulfoethyl)(meth)acrylamide, N-(1-methyl-2-sulfoethyl)

(meth)acrylamide, N-(2-methyl-3-sulfopropyl)(meth)acrylamide, N-(4-sulfobutyl)(meth)acrylamide, 10-sulfodecyl (meth)acrylate, styrenesulfonic acid, (meth)allylsulfonate, allylsulfonic acid, 3-(meth)acryloxy-2-hydroxypropylsulfonate, 3-(meth)acryloxyl-2-hydroxypropylsulfophenyl ether, 3-(meth)acryloxyl-2-hydroxypropyloxysulfobenzoate, 4-(meth)acryloxybutyl sulfonate, (meth)acrylamidomethyl sulfonic acid, (meth)acrylamidoethyl sulfonate, (meth)acrylamido-2-methylpropane sulfonate and the like.

The monomers having a carboxyl group are not critical in type and mention is made, for example, of (meth)acrylic acid, maleic acid, fumaric acid, glutaconic acid, itaconic acid, crotonic acid, sorbic acid, cinnamic acid, N-(meth)acryloyl glycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen maleate, 6-(meth)acryloyloxyethylnaphthalene-1,2,6-tricarboxylic acid, 0-(meth)acryloyl tyrosine, N-(meth)acryloyl tyrosine, N-(meth)acryloyl phenylalanine, N-(meth) acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid and the like.

The monomers having a phosphonate group are not critical in type and include, for example, phosphoxyethyl (meth)acrylate, 3-(meth)acryloxypropyl-3-phosphonopropionate, 3-(meth)acryloxypropylphosphonoacetate, 4-(meth)acryloxybutyl-3-phosphonopropionate, 4-(meth)acryloxybutylphosphonoacetate, 5-(meth)acryloxypentyl-3-phosphonopropionate, 5-(meth)acryloxypentylphosphonoacetate, 6-(meth)acryloxyhexyl-3-phosphonopropionate, 6-(meth)acryloxyhexylphosphonoacetate, 10-(meth)acryloxydecyl-3-phosphonopropionate, 10-(meth)acryloxydecylphosphonoacetate, 2-(meth)acryloxyethylphenylphosphonate, 2-(meth)acryloyloxyethylphosphonic acid, 10-(meth)acryloyloxydecylphosphonic acid, N-(meth)acryloyl-ω-aminopropylphosphonic acid and the like. The monomers may be used singly or in combination of two or more.

The weight average molecular weight of the polymer electrolyte having a negative charge according to the invention is not critical and is preferably at about 10,000 to about 1,000,000, more preferably at about 100,000 to about 700,000 and much more preferably at about 200,000 to about 500,000.

The polymer electrolyte having a positive charge is not critical so far as it has at least one cationic group, preferably two or more cationic groups. For instance, mention is made of: organic compounds having an N,N-dimethylaminoalkyl group at a side chain thereof; and polyethyleneimines and the like. These polymer electrolytes may be used singly or in admixture of two or more. Of these, there are preferably used poly(N,N-dimethylaminopropylacrylamide) having a weight average molecular weight of about 10,000 to about 1,000,000, poly(N,N-dimethylaminoethylacrylamide) having a weight average molecular weight of about 10,000 to about 1,000,000, and a polyethyleneimine having a weight average molecular weight of about 10,000 to about 1,000,000. More preferably, mention is made of poly(N,N-dimethylaminopropylacrylamide) having a weight average molecular weight of about 10,000 to about 500,000, poly(N,N-dimethylaminoethylacrylamide) having a weight average molecular weight of about 10,000 to about 500,000, and a polyethyleneimine having a weight average molecular weight of about 10,000 to about 500,000 (especially, about 100,000).

Alternatively, the polymer electrolyte having a positive charge may be obtained by polymerizing a monomer having a positive charge. Although not limitative, a monomer having a positive charge includes one having at least one functional group selected from an amino group (—NH2), an imino group (═NH, —NH—), an imidazoyl group, a pyridyl group and the like.

The monomer having an amino group is not critical and mention is made, for example, of (meth)allylamine, aminoethyl (meth)acrylate, aminopropyl (meth)acrylate, dimethylaminoethyl (meth)acrylate, diethylaminoethyl (meth)acrylate, methylethylaminoethyl (meth)acrylate, dimethylaminopropyl (meth)acrylate, dimethylaminostyrene, diethylaminostyrene, morpholinoethyl (meth)acrylate, lysine and the like.

The monomer having an imino group is not critical and mention is made, for example, of N-methylaminoethyl (meth)acrylate, N-ethylaminoethyl (meth)acrylate, N-t-butylaminoethyl (meth)acrylate, ethyleneimine and the like.

The monomer having an imidazoyl group includes 4-vinylimidazole, N-vinyl-2-ethylimidazole, N-vinyl-2-methylimidazole and the like.

The monomer having a pyridyl group includes 2-vinylpyridine, 4-vinylpyridine, 2-methyl-5-vinylpyridine and the like.

The above monomers may be used singly or in combination of two or more.

The weight average molecular weight of the polymer electrolyte having a positive charge according to the invention is not critical and is preferably at 10,000 to 1,000,000, more preferably at 100,000 to 500,000.

It will be noted that the polymer electrolyte according to the invention may have, aside from the monomer having a negative or positive charge, constituent units derived from other type of monomer. Other type of monomer is not critical and known monomers may be used therefor. More particularly, mention is made of: salts such as sodium salts, potassium salts and ammonium salts of the above-indicated monomers having a carboxyl group; monovalent metal salts, divalent metal salts, ammonium salts and organic amine salts of the above-indicated monomers having a sulfo group; (poly)alkylene glycol di(meth)acrylates such as triethylene glycol di(meth)acrylate, (poly)ethylene glycol di(meth)acrylate, polypropylene glycol di(meth)acrylate, (poly)ethylene glycol (poly)propylene glycol di(meth)acrylate and the like; difunctional (meth)acrylates such as hexanediol di(meth)acrylate, trimethylolpropane tri(meth)acrylate, trimethylolpropane di(meth)acrylate and the like; (poly)alkylene glycol dimaleates such as triethylene glycol dimaleate, polyethylene glycol dimaleate and the like; esters of unsaturated monocarboxylic acids and alcohols having 1 to 4 carbon atoms such as methyl (meth)acrylate, ethyl (meth)acrylate, propyl (meth)acrylate, glycidyl (meth)acrylate, methyl crotonate, ethyl crotonate, propyl crotonate and the like; amides of unsaturated monocarboxylic acids and amines having 1 to 30 carbon atoms such as methyl (meth)acrylamide and the like; vinylaromatic compounds such as styrene, α-methylstyrene, vinyltoluene, p-methylstyrene, and the like; alkane diol mono(meth)acrylates such as 1,4-butanediol mono(meth)acrylate, 1,5-pentanediol mono(meth)acrylate, 1,6-hexanediol mono(meth)acrylate and the like; dienes such as butadiene, isoprene, 2-methyl-1,3-butadiene, 2-chloro-1,3-butadiene and the like; unsaturated amides such as (meth)acrylamide, (meth)acrylalkylamide, N-methylol (meth)acrylamide, N,N-dimethyl (meth)acrylamide and the like; unsaturated nitriles such as (meth)acrylonitrile, α-chloroacrylonitrile and the like; unsaturated esters such as vinyl acetate, vinyl propionate and the like; and unsaturated amines such as aminoethyl (meth)acrylate, methylaminoethyl (meth)acrylate, dimethylaminoethyl (meth)acrylate, dimethylaminopropyl (meth)acrylate, dibutylaminoethyl (meth)acrylate, vinylpyridine and the like. These other types of monomers may be used singly or in combination of two or more. It will be noted that in case where the polymer electrolyte further contains constituent units derived from other type of monomer, the amount of other type of monomer is not critical so far as the amount is at a level not impairing an effect of such a monomer having a positive or negative charge as set out above. The amount of other type of monomer is preferably within a range of 1 to 10% by mass relative to all the monomers used.

The method of preparing a polymer electrolyte according to the invention is not critical and known polymerization processes can be used. In general, the preparation is possible by polymerizing the monomer indicated above by use of a polymerization initiator. The manner of polymerizing a monomer component is not critical and is feasible, for example, by a method of polymerization in solvent or bulk polymerization. If the polymer electrolyte and tacky polymer according to the invention are made of a block copolymer or graft copolymer, there can be exemplified, for example, living polymerization, polymerization using a macro monomer, polymerization using a high-molecular-weight polymerization initiator, polycondensation and the like although not limitative.

The respiratory region volume inhibitor of the invention is preferably made of a composition including a coating film-forming component as a main component, a coating film adjusting component and a solvent. The solvent may be one that is properly selected depending on the type of coating film-forming component to be used and is able to dissolve or disperse the coating film-forming component. Particularly, mention is made of: water; dimethylsulfoxide and dimethylformamide; glycols such as ethylene glycol, diethylene glycol, propylene glycol, triethylene glycol, polyethylene glycol, polypropylene glycol and the like; and fats and oils such as olive oil, castor oil, squalane, lanolin oil and the like. The above solvents may be used singly or in the form of a mixed solution of two or more.

If water is chosen as a constituent component of the respiratory region volume inhibitor, salt may be appropriately added to water so as to make a desired pH for use as a buffer solution.

Further, the coating film-adjusting component should preferably have an action of adjusting the viscosity of the respiratory region volume inhibitor of the invention, an action of controlling the surface tension and a capability of making a respiratory region volume foamy inhibitor of the invention. As an example of the coating film-adjusting component, mention is made of known surfactants, viscosity adjusters, known foaming agents and known defoaming agents. More particularly, mention is made of: nitrogen gas, helium gas, argon gas, carbon monoxide, carbon dioxide, carbonic acid gas, oxygen, and lower alcohols such as methanol, ethanol, isopropanol, butanol and the like; silicone compounds such as silicone oil; and organic polar compounds such as 2-ethylhexanol, diisobutyl carbinol, amyl alcohol, tributyl phosphate, sodium octylphosphate, metal salts of stearic acid, metal salts of palmitic acid, isoamyl stearate, polyethylene glycol, Miglyol, diglycol laurate, sorbitan trioleate, polyethylene glycol, polypropylene glycol, polyoxyethylene sorbitan monolaurate, Pluronic-nonionic surfactants, sodium hydrogen carbonate, citric acid, polyalkylene glycol and derivatives thereof, and the like. These coating film-adjusting components may be used singly or in the form of admixtures of two or more.

The respiratory region volume inhibitor of the invention is preferably in a foam. In this case, foaming may be made by introducing nitrogen gas, helium gas, argon gas, carbon monoxide, carbon dioxide, carbonic acid gas or oxygen as the coating film-adjusting component. Alternatively, sodium hydrogen carbonate or citric acid may be added, as the coating film-adjusting component, to the respiratory region volume inhibitor of the invention. Especially, it is preferred to prepare a respiratory region volume foamy inhibitor by dispersing sodium hydride or citric acid in the form of powder. It will be noted that the preparation of the respiratory region volume foamy inhibitor is not limited to above method.

The external stimulation responsive to the film-forming component according to the invention may be contained as an external stimulation component in the respiratory region volume inhibitor of the invention. As an external stimulation, mention is made of temperature, pH, light, electric field, magnetic field, chemical substance and the like. The external stimulation component according to the invention is appropriately selected depending on the film-forming component used and preferably includes water, divalent metal ions, reactive gases or polymer electrolytes. It is to be noted that the polymer electrolyte may be those polymer electrolytes of the invention set out before.

The divalent metal ions include calcium ions, magnesium ions, barium ions, iron ions, copper ions or the like. In practice, mention is made of those solutions, dissolved in water, of compounds capable of generating divalent metal ions in solution and including, for example, calcium chloride, calcium hydrogen phosphate, calcium dihydrogen phosphate, tricalcium phosphate, calcium sulfate, calcium hydroxide, magnesium chloride, barium chloride and the like.

For the reactive gas, no limitation is placed thereof although the gas is appropriately selected depending on the type of stimulation responsive component used. For instance, when taking a uniform coating of a polymer electrolyte on a surface of the pulmonary alveolar parenchyma into account, it is preferred to use a gas which is less viscid than the polymer electrolyte introduced. For example, mention is made of air, oxygen, carbon dioxide, carbon monoxide, nitrogen, helium gas, argon gas or the like.

The coating film-forming component according to the invention preferably contains a tacky polymer and a reactive gas used as the external stimulation component. Where a tacky polymer is chosen as the coating film-forming component, water or dimethylsulfoxide is preferably selected among from the above-indicated solvents, of which water is more preferred. These are excellent in safety.

The coating film-forming component according to the invention is preferably such that polymer electrolyte (A) is contained, and the external stimulation component is constituted of polymer electrolyte (B), or polymer electrolyte (B) and polymer electrolyte (A). In other words, where a polymer electrolyte is selected as the coating film-forming component, the external stimulation component contains a polymer electrolyte other than the first-mentioned polymer electrolyte and having a charge different in sign from the polymer electrolyte selected as the coating film-forming component. In this sense, in the invention, the charge of polymer electrolyte (A) and the charge of polymer electrolyte (B) differ in sign from each other. Hence, the above-indicated monomers should be appropriately selected in such a way that the electric charges of polymer electrolytes (A) and (B) differ from each other to prepare the polymer electrolytes (A) and (B), respectively. Polymer electrolytes (A) and (B) are selected from the polymer electrolytes exemplified above.

When polymer electrolyte (A) is used for the coating film-forming component and polymer electrolyte (B) is for the external stimulation component as set out above, these electrolytes mutually associate by an electrostatic action between polymer electrolytes (A) and (B) to form a so-called ion complex coating film over and in intimate contact with the entire surface of the inner walls of the respiratory region. This ion complex coating film establishes a closed system thereof except for the injection port of the respiratory region volume inhibitor thereby forming a balloon-shaped closed pouch constituted of the coating film. Hence, when air is removed from within the balloon-shaped closed pouch, the volume of the pulmonary alveolar parenchyma can be reduced readily, efficiently and rapidly.

Preferably, the respiratory region volume inhibitor according to the invention is independently provided with a first coating film-forming component containing polymer electrolyte (A) serving as a coating film-forming component, a solvent and a film adjusting component, and an external stimulation component containing polymer electrolyte (B) serving as an external stimulation component, a solvent and a film adjusting component. Further, a second coating film-forming component containing polymer electrolyte (A) serving as a coating film-forming component, a solvent and a film adjusting component may also be provided. In this case as well, it is preferred that these components are independently provided without mixing thereof.

The compositional ratio of the coating film-forming component in the above-described case is preferably such that 5 to 25 parts by mass of the coating film adjusting component and 75 to 95 parts by mass of the solvent are used per 100 parts by mass of the coating film-forming component. The compositional ratio of the external stimulation component is preferably such that 5 to 25 parts by mass of the coating film adjusting component and 75 to 100 parts by mass of the solvent are used per 100 parts by mass of the external stimulation component.

The mixing ratio between polymer electrolyte (A) and polymer electrolyte (B) is not critical. The mixing ratio (ratio of mass) between polymer electrolyte (A) and polymer electrolyte (B) is preferably at 1:0.1 to 5, more preferably at 1:0.5 to 2. Such a mixing ratio enables polymer electrolyte (A) and polymer electrolyte (B) to be efficiently reacted with each other, thereby forming an ion complex coating film over the entire surface of the inner walls of the emphysema-suffering pulmonary alveolar parenchyma.

It will be noted that it is preferred that the first coating film-forming component, the second coating film-forming component and the external stimulation component are independently, individually injected into the respiratory region, respectively, although this is described in detail with respect to a method of using the respiratory region volume inhibitor of the invention appearing hereinafter.

In case where polymer electrolytes are selected as the coating film-forming component, polymer electrolyte (A) or polymer electrolyte (B) may be injected into the respiratory region as they are, or may be used in a state of being dissolved or dispersed in an appropriate solvent. The solvent usable in the latter case is not critical so far as it is able to dissolve or disperse polymer electrolyte (A) or polymer electrolyte (B) and is safe. For instance, mention is made of: water; dimethyl sulfoxide and dimethylformamide; glycols such as ethylene glycol, diethylene glycol, propylene glycol, triethylene glycol, polyethylene glycol, polypropylene glycol and the like; and fats and oils such as olive oil, castor oil, squalane, lanoline and the like. These solvents may be used singly or in the form of a mixed solution of two or more. Of the solvents, water, dimethyl sulfoxide and dimethylformamide are preferred, among which water is more preferred. These are excellent in safety.

If a film-forming polymer precursor is selected as the coating film-forming component according the invention, it is preferred to use water as the external stimulation. If a tacky polymer is selected as the coating film-forming component according to the invention, divalent metal ions are preferably used.

In case where a material (stimulation responsive material) capable of film formation (curing) by reaction with divalent metal ions is used as the film-forming component, the material can react (cure) with calcium ions or the like existing on the surface of the emphysema-suffering pulmonary alveolar parenchyma thereby forming a coating film. Alternatively, prior to injection of the material into the respiratory region, a solution having divalent metal ions may be preliminarily injected into the respiratory region via a catheter or the like. This enables the film formation to be promoted. The solution having divalent metal ions is not critical so far as it can initiate the reaction (curing) with the material and it is able to block collateral channels if present, and can be appropriately selected depending on the type of the material. More particularly, combinations of the material and the solution having divalent metal ions include a solution dissolving, in water, alginic acid and a compound capable generating, in solution, divalent metal ions such as calcium ions, magnesium ions, barium ions or the like. The compound, for example, includes calcium chloride, calcium hydrogen phosphate, calcium dihydrogen phosphate, tricalcium phosphate, calcium sulfate, calcium hydroxide, magnesium chloride, barium chloride or the like. Of these, a solution dissolving, in water, alginic acid and a compound capable of generating calcium ions in the solution is preferred. In this case, alginic acid and a calcium compound undergo crosslinkage reaction (egg-box structure) and are gelled to efficiently form a coating film on the inner walls of the emphysema-suffering pulmonary alveolar parenchyma.

The respiratory region volume inhibitor according to the invention is preferably such that a coating film-forming component is made of a film-forming polymer precursor or a tacky polymer, and a film adjusting component is further contained and the external stimulation is made of water or divalent metal ions.

The respiratory region volume inhibitor according to the invention may contain the coating film-forming component alone as an effective component or may further contain other types of components. Other types of components include those necessary for drug formulation, for which there may be appropriately used additives, which have been employed in the pharmaceutical field and are pharmaceutically acceptable, such as a carrier, buffering agent, preservative, antioxidant and the like. The content of these additives can be appropriately determined by those skilled in the art.

A method of using the respiratory region volume inhibitor according to the invention is now described in detail.

The method of using the respiratory region volume inhibitor according to the invention against pulmonary emphysema includes: a step (a) of inserting a catheter into a bronchus or bronchiole; a step (b) of injecting a respiratory region volume inhibitor via the catheter into a respiratory region including pulmonary alveoli or alveolar sacs to form a coating film on inner walls of the respiratory region; and a step (c) of shrinking the pulmonary alveoli or alveolar sacs. It will be noted that the method of using the respiratory region volume inhibitor in this specification means the use of the inhibitor drug for the purpose of treating the pulmonary emphysema, and the term "treating" means medical practice for the purpose of curing, alleviating, relieving, repairing, preventing or improving the pulmonary emphysema, emphysema symptoms or a disease state secondary to the pulmonary emphysema.

The invention is now described in detail with reference to the drawings.

Figure 1B:
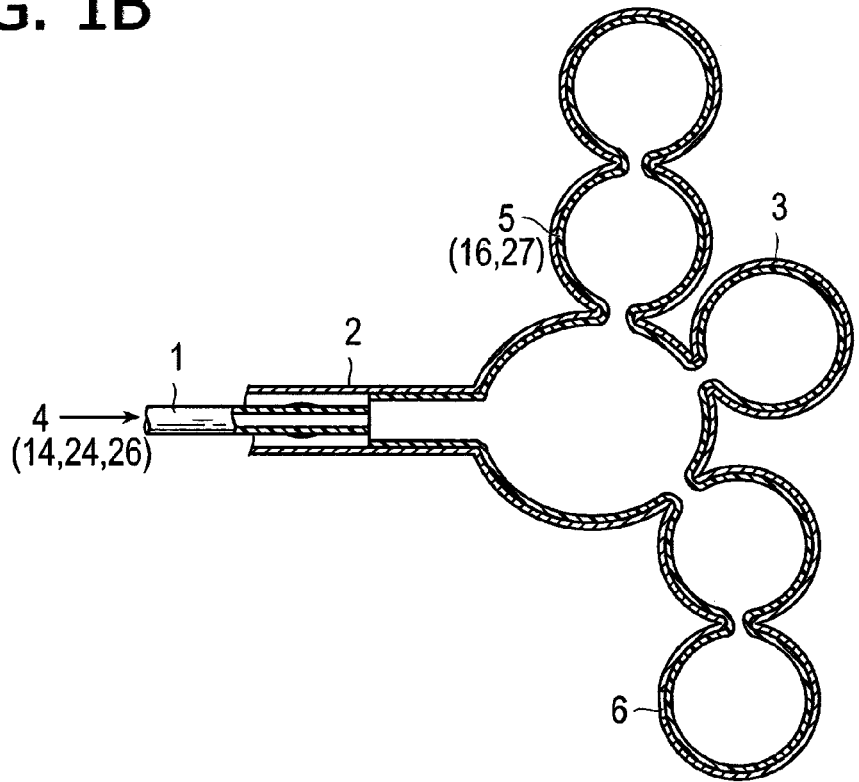
FIG. 1B is a schematic sectional view showing a step in sequence of the method of the invention.
Figure 1C:
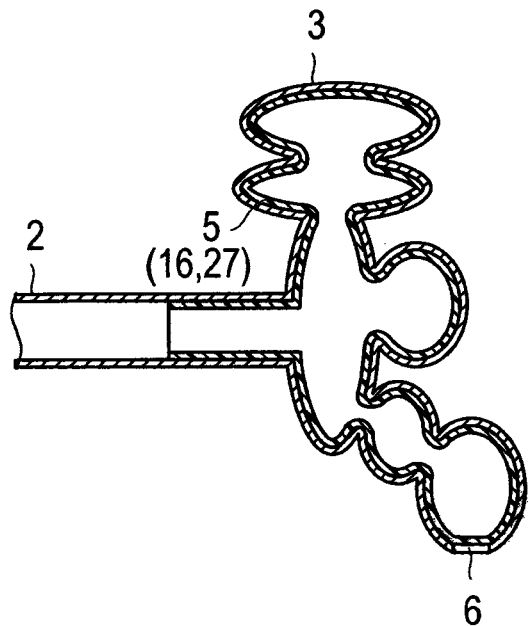
FIG. 1C is a schematic sectional view showing a further step of the method of the invention.

FIGS. 1A to 1C are, respectively, a schematic sectional view showing a step sequence of the method of the invention. More particularly, according to the method of using the respiratory region volume inhibitor of the invention, as shown in FIGS. 1A and 1B, a catheter 1 is inserted into a bronchus or bronchiole 2 [step (a)]. A respiratory region volume inhibitor 4 (14, 24, 26) is injected into a respiratory region including pulmonary alveoli or alveolar sacs 3 via the catheter to form a coating film 5 (16, 27) on inner walls of the respiratory region [step (b)], followed by shrinking the pulmonary alveoli or alveolar sacs [step (c)]. The respective steps are described in detail below although the steps should not be construed as limited to the following ones.

1. Step (a)

In this step, the catheter is inserted into the bronchus or bronchiole. In more detail, as shown in FIGS. 1A, 2A, 3A and 4A, the catheter 1 is inserted into the bronchus or bronchiole 2 leading to the respiratory region including the emphysema-suffering pulmonary alveoli or alveolar sacs (which may be hereinafter referred to simply as "emphysema-suffering pulmonary alveolar parenchyma") 3.

No limitation is specifically placed on the type of the catheter, which is appropriately selected depending on the diameter (number of branches) of the bronchus or bronchiole to be introduced. More particularly, there can be used known respiratory, cardiovascular and gastrointestinal catheters used in medical applications. No limitation is also placed on the structure of the catheter, which may have either a balloon-bearing structure or a balloon-free structure. When taking the ease in transfer to inside a trachea and sealing property into account, a balloon-bearing structure is preferred. The number of lumens of the catheter is not critical and is appropriately selected depending on the number of materials used in the steps (b) and (c) and the presence or absence of balloon as will be described hereinafter.

Figure 5A:
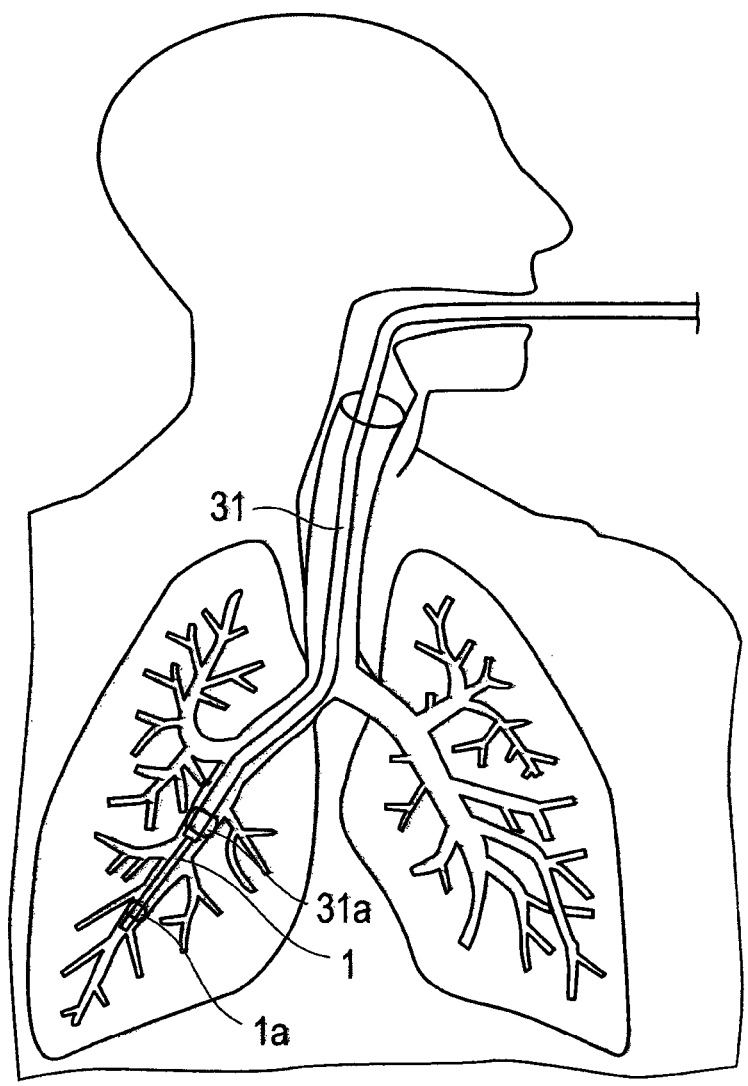
FIG. 5A is a schematic sectional view showing a preferred embodiment in the step (a) of the method of the invention.
Figure 5B:
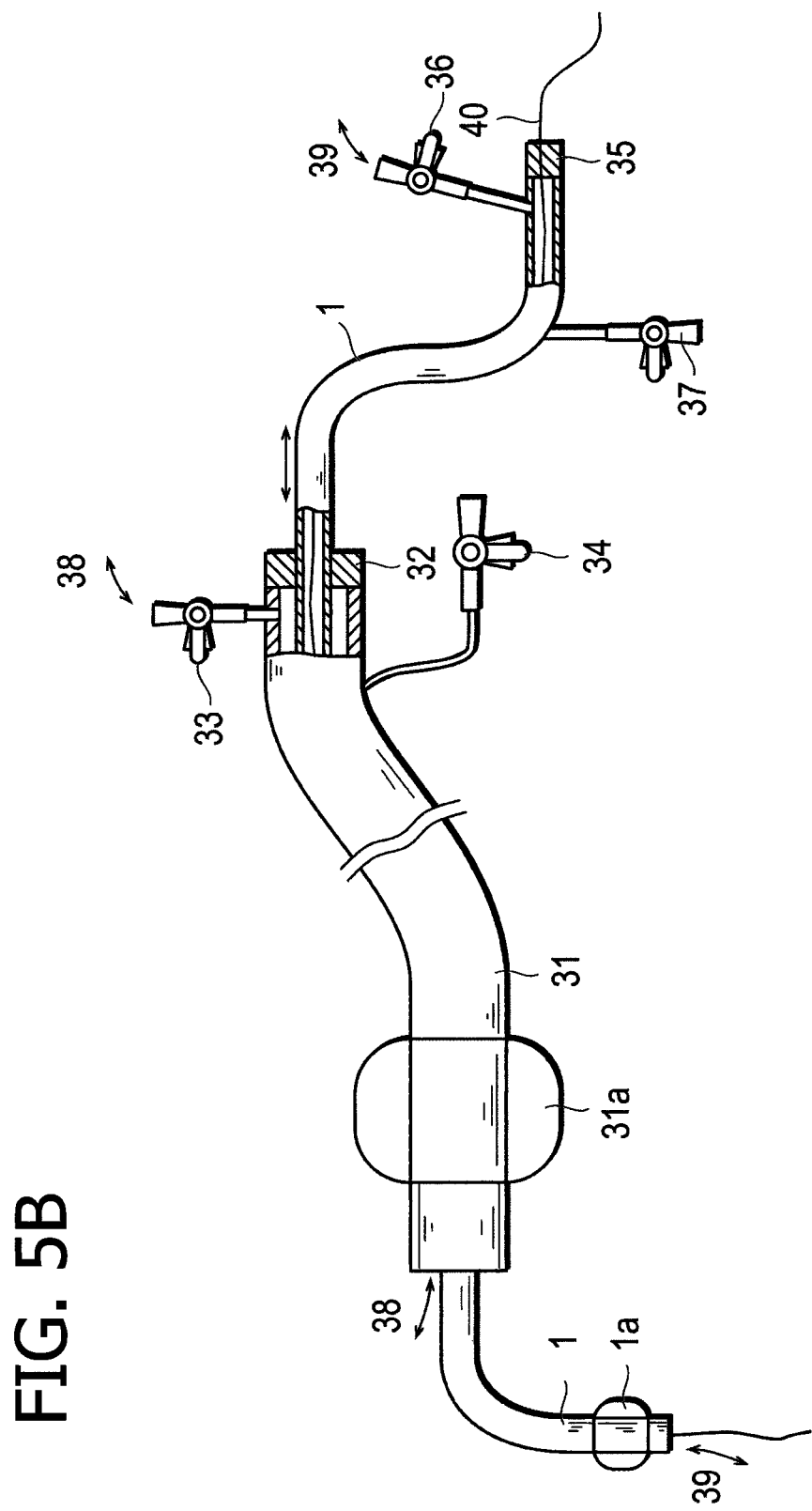
FIG. 5B is a schematic sectional view showing preferred embodiment in the step (a) of the method of the invention.

In case where the catheter 1 is inserted into the emphysema-suffering pulmonary alveolar parenchyma 3, the catheter 1 may be passed through a sheath 31 located at a more proximal portion as shown in FIG. 5A. The structure of the sheath 31 is not critical and may have a balloon or may be free of a balloon. It is preferred to have a balloon 31a capable of blocking the bronchus or bronchiole. A schematic view of the structures of the sheath 31 and the catheter 1 favorably usable in the invention is shown in FIG. 5B. On this occasion, no specific limitation is placed on set positions, in the bronchus or bronchiole, of the balloon 31a attached to the sheath 31 and a balloon 1a attached to the catheter 1. Preferably, the balloon 31a attached to the sheath 31 is set at the bronchus, and the balloon 1a attached to the catheter 1 is set at a more terminal side of the bronchus, particularly at the bronchiole. In this way, when the bronchus or bronchiole is blocked with the balloon 31a, it becomes possible to increase air tightness at a more distal side than the sheath, thus enabling the emphysema-suffering pulmonary alveolar parenchyma to be more effectively treated with the catheter. The blockage at different sites of the bronchus or bronchiole with both of the balloons 1a and 31a permits a pressure between the balloons 1a and 31a (e.g. a normal pulmonary alveolar parenchyma) and a pressure at a more peripheral side (e.g. the emphysema-suffering pulmonary alveolar parenchyma) than the balloon 1a to be easily controlled, respectively.

The blockage in the bronchus or bronchiole with the balloon 31a enables ventilation to be maintained by application of a respiratory pressure at a more proximal side than the balloon 31a, thereby ensuring an efficient and safe treatment. Although an inflation and deflation method of the balloon 31a is not critical, this may be carried out by use of a three-way stopcock 34 disposed at a base end side of the sheath 31.

Further, when a pressure at a more distal portion than the balloon 31a attached to the sheath 31 is held constant, the operation at a tip end side ahead of the catheter 1 can be stabilized. For one instance, when the bronchus or bronchiole is blocked with the balloon 31a to reduce a pressure at the more distal portion than the sheath 31 to increase the degree of attachment of walls of the bronchus or bronchiole to the balloon 1a attached to the catheter 1 and prevent a gas from flowing from a collateral channel to a more distal portion than the catheter 1, pressure reduction at the more distal portion than the catheter is made easy. In the course of injection of a drug at a constant pressure into the more distal portion than the catheter 1, when a pressure at the more distal portion than the sheath 31 is made smaller than a drug injection pressure and is kept constant, the drug can be efficiently delivered. The manner of controlling a pressure at a tip end (peripheral) side ahead of the sheath 31 and at a tip end (peripheral) side ahead of the catheter 1 is not critical. More particularly, as shown in FIG. 5B, a seal valve 32 is provided at the base end side of the sheath 31, and the catheter 1 is inserted into the sheath 31 via the seal valve 32. The provision of the seal valve 32 in this way permits the inside of the pulmonary alveolar parenchyma at the tip end (peripheral) side ahead of the sheath 31 to be formed as a closed system. Thus, the pressure control at the site can be easily performed. When a three-way stopcock 33 is provided at a base end portion of the sheath 31 and a gas 38 is introduced or suctioned from the three-way stopcock 33, the pressure inside the pulmonary alveolar parenchyma at the tip end (peripheral) side ahead of the sheath 31 can be controlled. The manner of controlling a pressure at the tip end (peripheral) side ahead of the catheter 1 may also be performed in a similar way. More particularly, as shown in FIG. 5B, a seal valve 35 is provided at a base end side of the catheter 1. The provision of the seal valve 35 in this way enables the inside of the pulmonary alveolar parenchyma at the tip end (peripheral) side ahead of the catheter 1 to be formed as a closed system. Hence, the pressure control at the site can be easily controlled. When a three-way stopcock 36 is provided at the base end side of the catheter 1 and a gas or liquid 39 is introduced or suctioned from the three-way stopcock 36, the pressure inside the pulmonary alveolar parenchyma at the tip end (peripheral) side ahead of the catheter 1 can be controlled. Although the manner of inflating or deflating the balloon 1a is not critical, this can be performed by use of a three-way stopcock 37 provided at the base end side of the catheter 1. For the purpose of permitting easy insertion of the catheter 1 into a desired position, the catheter 1 may have a lumen for introducing a guide wire 40.

For instance, there is used a catheter which is a type of the catheter 1 provided with the balloon 1a for blocking the bronchus and which is provided with openings at a distal portion side and a proximal portion side and also provided with a lumen capable of feeding a fluid toward the distal portion side, or an OTW-PTCA catheter that is used for stenotic treatment of an intravascular lumen in a cardiac blood vessel region. As a catheter, there may be used commercially available ones including, for example, a microcatheter (e.g. FINECROSS (registered trade name), made by Terumo Corporation) used for passing a guide wire through a narrowed intravascular lumen in the cardiac blood vessel region, PTCA catheter (e.g. Ryujin Plus OTW (registered trade name), made by Terumo Corporation) and the like. Although the catheter described above can be inserted from a working lumen of a bronchoscope into a bronchial lumen, the use of the bronchoscope is not essential if the catheter can be located at an arbitrary position. The outer diameter of the catheter 1 or the balloon 1a under inflation is not critically limited and is appropriately selected depending on the diameter of the bronchus or bronchiole 2. More particularly, the outer diameter of the balloon 1a under inflation preferably has a size slightly larger than the inner diameter of the bronchus or bronchiole 2 communicating with tissues of an arbitrary pulmonary alveoli or alveolar sac (air sac) to be inserted and coated with. More preferably, the outer diameter [Y (mm)] of the balloon 1a under inflation is about one to double the inner diameter [X (mm)] of the bronchus or bronchiole 2. In this case, the bronchus or bronchiole formed of elastic smooth muscles can be pressure-attached to the catheter or a balloon portion without undergoing excess damage. In addition, removal efficiency can be increased in case where the respiratory region volume inhibitor 4 is discharged from the respiratory region as will be described hereinafter.

In this step, a guide wire may be inserted into a lumen (e.g. fluid supply lumen) of the catheter so as to introduce the catheter into the bronchus or bronchiole 2. This enables the operation to be performed while keeping such a positional relationship that a tip end of the guide wire is located at a more peripheral side than a tip end of the catheter. Thus, the tip end portion of the catheter can be guided closely to a tissue of the alveolar sac (air sac) or pulmonary alveolus at a more peripheral side than the bronchus or bronchiole 2. The guide wire may be any of known respiratory, cardiovascular and gastrointestinal guide wires used in medical applications, and its outer diameter can be appropriately selected depending on the size of the catheter lumen used. More particularly, there can be used guide wires used for the treatment of a cardiac blood vessel including, for example, a guide wire (hereinafter referred to as GW) of Runthrough (registered trade name)(outer diameter: 0.014 inches, made by Terumo Corporation).

It is preferred that a contrast member is set at the tip end portion of the guide wire or at the tip end of the catheter. Under X-ray fluoroscopic observation, the tip end positions of the guide wire and the catheter projecting from a tip end of an endoscope can be understood and lead to a respiratory region including preliminarily specified, emphysema-suffering pulmonary alveoli or alveolar sacs through X-ray fluoroscopy or CT imaging. In this case, after confirming that the tip end of the catheter has arrived at an intended site by X-ray fluoroscopy, the guide wire is removed. It is preferred that the operation is performed while keeping such a positional relationship that the tip end of the guide wire is located at a more peripheral side than the tip end of the catheter. Additionally, it is preferred that the tip end of the catheter has such a structure as to suppress or prevent the inner walls of the respiratory region including the pulmonary alveoli or alveolar sacs from being attached thereto, such as a meshwork structure or a plurality of pores.

2. Step (2)

In this step, a respiratory region volume inhibitor is injected into the respiratory region including the pulmonary alveoli or alveolar sacs via the catheter to form a coating film on the inner walls of the respiratory region. According to this step, even if there exists a collateral channel (reference numeral 6 in FIG. 1A) in the emphysema-suffering pulmonary alveolar parenchyma, there is formed a coating film, which is a balloon-shaped, closed pouch formed of the respiratory region volume inhibitor, over the entire surface of the inner walls including the collateral channel of the emphysema-suffering pulmonary alveolar parenchyma. More particularly, according to this step, the emphysema-suffering pulmonary alveolar parenchyma becomes a closed system therein except for a communication port with the bronchus or bronchiole (FIG. 1B). Accordingly, when the pulmonary alveolar parenchyma is shrunk in a next step, there occurs little or no leakage of air from the emphysema-suffering pulmonary alveolar parenchyma, so that the air in the closed system can be reliably removed to efficiently reduce the volume of the pulmonary alveolar parenchyma. The formation of such a coating film acts to recover the elasticity of the emphysema-suffering pulmonary alveolar parenchyma. Thus, lung hyperinflation can be alleviated or suppressed. It will be noted that the "respiratory region" used herein is a collective term of respiratory organs located at a more distal side than the bronchi including the respiratory bronchiole and two alveoli. More specifically, the respiratory region includes bronchi, bronchiole, terminal bronchiole, respiratory bronchiole, alveolar duct (alveolar path), pulmonary alveoli, alveolar sacs, pulmonary vein and pulmonary artery, and preferably includes respiratory bronchiole, alveolar duct (alveolar path), pulmonary alveoli, alveolar sacs and pulmonary vein.

The respiratory region volume inhibitor is injected into the respiratory region including pulmonary alveoli or alveolar sacs, particularly the emphysema-suffering pulmonary alveolar parenchyma, via a catheter. On this occasion, it is preferred that as shown in FIG. 2B, the catheter 1 having the balloon 1a is used and the balloon 1a is inflated prior to injection of the respiratory region volume inhibitor 4 to block the bronchus or bronchiole 2. More particularly, it is preferred that the method of the invention makes use of a catheter having a balloon and further includes, in the step (b), inflating the balloon prior to injection of the respiratory region volume inhibitor to block the bronchus or bronchiole. According to such an operation as set out above, the respiratory region volume inhibitor 4 is suppressed or prevented from flowing backward to the tracheal (proximal) side of the bronchus or bronchiole thereby permitting the respiratory region volume inhibitor 4 to efficiently contact the desired emphysema-suffering pulmonary alveolar parenchyma 3. The manner of inflation of the balloon 1a of the catheter 1 is not critical, for which known methods can be used. For instance, there can be used a method wherein the balloon 1a of the catheter 1 is inflated by use of a syringe or indeflator connected to an inflation lumen of a balloon unit arranged at a base end portion of the catheter. An infill used for balloon inflation is not critical and mention is made of air, a contrast agent, a contrast agent-containing physiological saline solution and the like. Of these, it is preferred to use a gas, particularly, carbonic acid gas or oxygen, when taking disease complications, such as pneumonia, into account.

This is because if the balloon is broken down to generate leakage, safety is ensured. The set position of the balloon is not critical. For example, the balloon can be either set at a distal terminal end of the catheter or set at a tracheal (proximal) side from the distal terminal end of the catheter. In case where the tip end of the catheter is located within the bronchus, it is preferred to set the catheter in such a way that the balloon does not pass over a branch at the proximal side of the bronchus.

It is also preferred that after the injection of air into the respiratory region via a catheter, the respiratory region volume inhibitor is injected. As stated above, it is usual that a collateral channel does not exist in the normal pulmonary alveolar parenchyma or is very small in number if present. Hence, when air is injected into the respiratory region, the normal pulmonary alveolar parenchyma is filled with air, under which if a respiratory region volume inhibitor is subsequently injected, little respiratory region volume inhibitor enters into the pulmonary alveolar parenchyma. Even in the latter case, only a very small number of collateral channels exist, so that a ratio occupied by the normal pulmonary alveolar parenchyma to be introduced with the respiratory region volume inhibitor is very small and thus, the influence by such injection is negligible. In contrast thereto, pores called collateral channels connecting with peripheral pulmonary alveoli exist in the emphysema-suffering pulmonary alveolar parenchyma. Accordingly, if air is injected into the respiratory region, the air leaks from the collateral channels, so that when a respiratory region volume inhibitor is injected, it readily enters into the emphysema-suffering pulmonary alveolar parenchyma. Therefore, such an operation as set out above allows the respiratory region volume inhibitor to be selectively injected into the emphysema-suffering pulmonary alveolar parenchyma having collateral channels therein. On this occasion, the injection pressure of air is not critical so far as it is one sufficient not to substantially damage the normal and emphysema-suffering pulmonary alveolar parenchymas and to adequately fill air in the normal pulmonary alveolar parenchyma. When the normal pulmonary alveolar parenchyma is filled with air, the injection pressure of air measured on the hand side rises. Accordingly, while measuring the air injection pressure, air is injected so that if the injection pressure rises, the injection speed may be reduced or the injection may be stopped.

In the course of the injection of a respiratory region volume inhibitor after injection of air into the respiratory region via a catheter, the injection pressure of air and the injection pressure of the respiratory region volume inhibitor may be the same or different. Preferably, the air injection pressure and the injection pressure of the respiratory region volume inhibitor are substantially the same. This permits a pressure in the normal pulmonary alveolar parenchyma and an injection pressure of the respiratory region volume inhibitor to be substantially the same. Hence, it can be prevented that the respiratory region volume inhibitor is injected into the normal pulmonary alveolar parenchyma or air is leaked from the normal pulmonary alveolar parenchyma. In contrast, the air pressure in the emphysema-suffering pulmonary alveolar parenchyma is smaller than the injection pressure of the respiratory region volume inhibitor, under which when injected, the respiratory region volume inhibitor selectively, efficiently enters into the emphysema-suffering pulmonary alveolar parenchyma.

Therefore, it is preferred to inject air into the respiratory region via catheter and subsequently inject the respiratory region volume inhibitor while maintaining the injection pressure.

In order to prevent an influence based on a variation in pressure of the lungs surrounding a target region, it is preferred that lung ventilation around the target region is transiently stopped to keep the pressure constant. The pressure on this occasion is preferably smaller than the injection pressure of the catheter 1. For instance, the constant pressure may be held at a continuous positive pressure or held open to atmospheric pressure. In particular, a bronchus or bronchiole at a more central side than a target bronchus or bronchiole is blocked with a balloon, and the catheter 1 can be inserted into the target bronchus or bronchiole while keeping the pressure constant. Although a site of the more central side bronchus to be blocked may be central trachea, it is more preferred to block a main bronchus or a peripheral side thereof thereby permitting the ventilation of the remaining portions to be continued. More particularly, as shown in FIG. 5A, a sheath 31 is set at a more proximal side than the catheter 1 to be inserted into the emphysema-suffering pulmonary alveolar parenchyma 3. When the balloon 31a attached to the sheath 31 is blocked, the pressure (pressure 1) of bronchi and bronchioles between the balloons 1 and 31a (e.g. a normal pulmonary alveolar parenchyma) can be held at a level smaller than an injection pressure (pressure 2) of the catheter 1 (pressure 1<pressure 2), preferably held at a continuous positive pressure or open to atmospheric pressure. On the other hand, when the balloon 1a attached to the catheter 1 is blocked, the respiratory region volume inhibitor 4 does not flow backward to the tracheal (proximal) side of the bronchi or bronchioles and can thus be efficiently contacted with the desired emphysema-suffering pulmonary alveolar parenchyma 3. The manner of controlling the pressure (pressure 1) of the bronchi and bronchioles between the balloons 1a and 31a (e.g. a normal pulmonary alveolar parenchyma) and the injection pressure (pressure 2) of the catheter 1 is not specifically limited. Preferably, as shown in FIG. 5B, a seal valve 32 is provided at the base end side of the sheath 31, and the catheter 1 is inserted into the sheath 31 via the seal valve 32. The provision of the seal valve 32 in this way enables an inner portion of the pulmonary alveolar parenchyma at a more tip (terminal) side than the sheath 31 to be formed as a closed system, so that the pressure control of the site can be easily performed. When a three-way stopcock 33 is provided at the base end portion of the sheath 31 and a gas 38 is introduced or suction from the three-way stopcock 33, the pressure (pressure 1) of the bronchus or bronchiole between the balloons 1a and 31a (e.g. a normal pulmonary alveolar parenchyma) is controlled conveniently or preferably at a continuous positive pressure or by opening to atmospheric pressure. The injection pressure of the catheter 1 can be likewise controlled. More particularly, as shown in FIG. 5B, a seal valve 35 is provided at the base end side of the catheter 1. The provision of the seal valve 35 in this way enables a gas to be selectively, readily filled in the closed system of the normal pulmonary alveolar parenchyma. Moreover, when a three-way stopcock 36 is provided at the base end side of the catheter 1 and a gas 39 is introduced or suctioned from the three-way stopcock 36, the injection pressure (pressure 2) of the catheter 1 can be appropriately controlled.

In this step, a respiratory region volume inhibitor is injected into the respiratory region including pulmonary alveoli or alveolar sacs to form a coating film on the inner walls of the respiratory region. On this occasion, the manner of forming the coating film is not critical. For instance, the methods (b-1) to (b-3) are preferably used.

(b-1) Method of injecting a respiratory region volume inhibitor as the above-described respiratory region volume inhibitor into the respiratory region through the catheter and removing excess respiratory region volume inhibitor by suction;

(b-2) Injecting, as the above-described respiratory region volume inhibitor, a material capable of being cured by reaction with water or divalent metal ions into the respiratory region via the catheter and removing the material by suction after reaction with water or the divalent metal ions present on the surface of the respiratory region; or (b-3) Method of injecting a first coating film-forming component containing polymer electrolyte (A) into the respiratory region via the catheter and subsequently removing excess polymer electrolyte (A) by suction to form a coated film of polymer electrolyte (A) on the inner walls of the respiratory region, further injecting an external stimulation component containing polymer electrolyte (B) whose charge is opposite to that of polymer electrolyte (A) into the respiratory region via the catheter to bring it into contact with polymer electrolyte (A), subsequently removing excess polymer electrolyte (B) by suction, and, if necessary, injecting a second coating film-forming component containing polymer electrolyte (A) into the respiratory region via the catheter after removal of polymer electrolyte (B) by suction and removing excess polymer electrolyte (A) by suction (wherein the first and second coating film-forming components each containing polymer electrolyte (A) and the external stimulation component containing polymer electrolyte (B) are used as the above-described respiratory region volume inhibitor).

Preferred methods of (b-1) and (b-3) are described in detail although the invention is not limited to those methods.

2-1. Step (b-1)

Figure 2A:
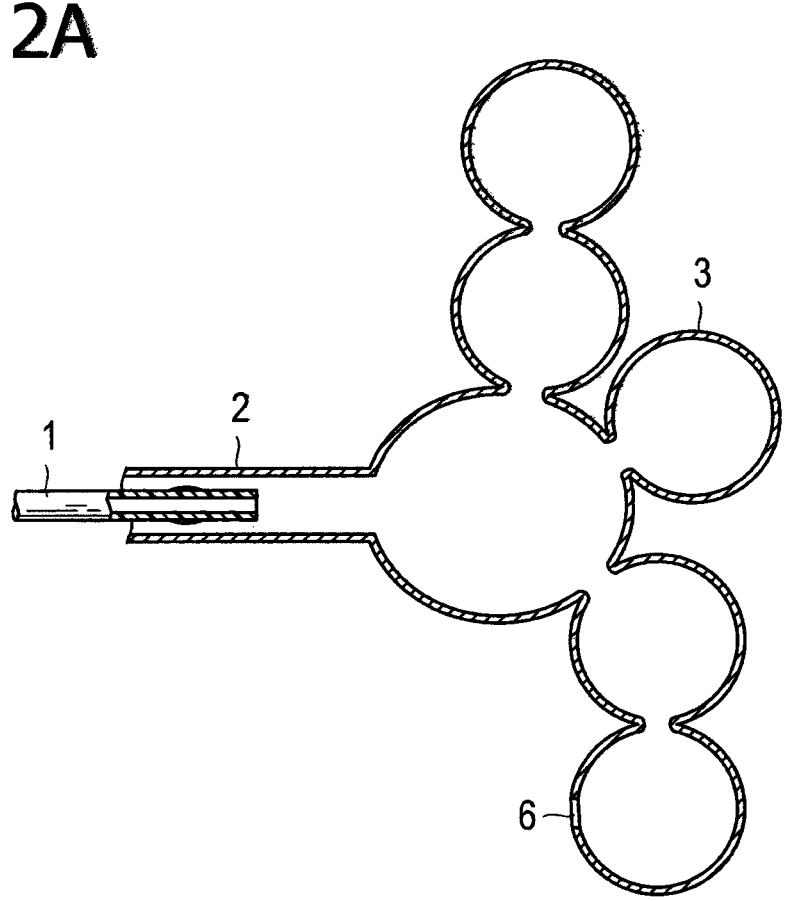
FIG. 2A is a schematic sectional view showing a step in sequence according to a first preferred embodiment of the method of the invention.
Figure 2B:
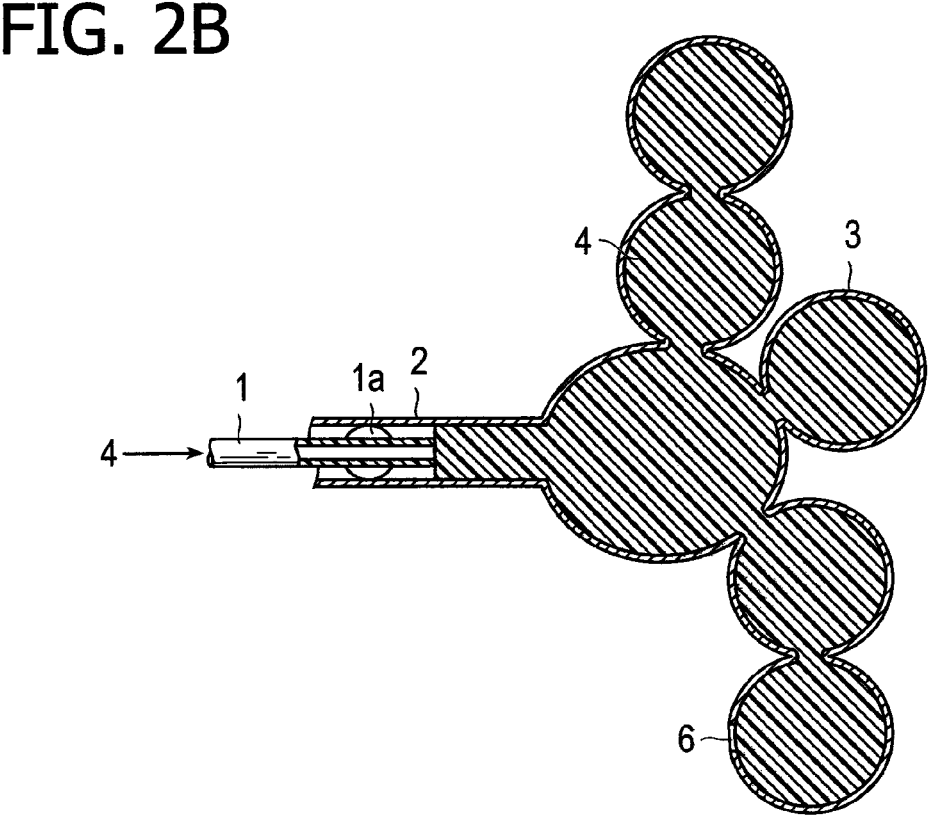
FIG. 2B is a schematic sectional view showing a step in sequence according to the first preferred embodiment of the method of the invention.
Figure 2C:
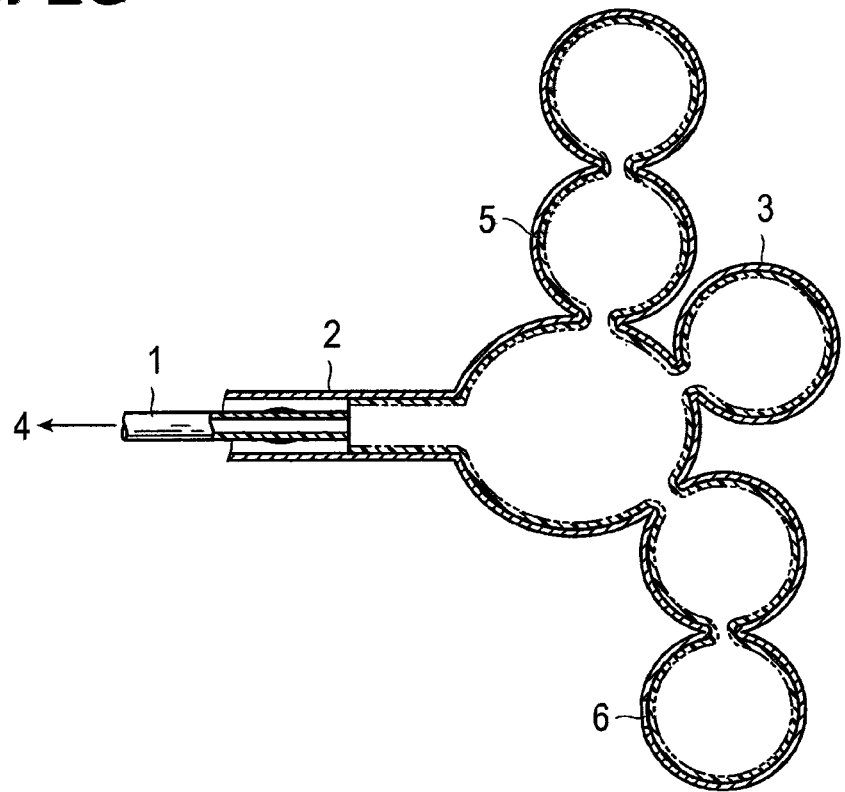
FIG. 2C is a schematic sectional view showing a step in sequence according to the first preferred embodiment of the method of the invention.

In this step, as shown in FIGS. 2B and C, a respiratory region volume inhibitor 4 serving as the respiratory region volume inhibitor is injected into a respiratory region including a bronchus or bronchiole 2 and pulmonary alveoli or alveolar sacs 3 via a catheter 1 (FIG. 2B), after which excess respiratory region volume inhibitor 4 is removed by suction (FIG. 2C). It will be noted that in the course of injecting the respiratory region volume inhibitor or removing excess solution of the respiratory region volume inhibitor by suction, it is preferred to inflate the balloon 1a and seal the catheter 1 and the inner walls of the bronchus or bronchiole 2 therebetween. This ensures reliable removable by suction of injection of the respiratory region volume inhibitor or removal by suction of excess solution of the respiratory region volume inhibitor.

The respiratory region volume inhibitor 4 has stickiness and when its solution is removed by suction, a thin coating film 5 of the solution is formed on the inner walls of the respiratory regions (an emphysema-suffering pulmonary alveolar parenchyma in the FIG. 3. If a collateral channel 6 exists in the emphysema-suffering pulmonary alveolar parenchyma 3, the collateral channel is usually a small-sized pore and the coating film 5 is formed to cover the collateral channel 6. In this way, according the above operation, the emphysema-suffering pulmonary alveolar parenchyma 3 forms a closed system except for a communication port with the bronchus (FIG. 2C). In doing so, no leakage of air through the collateral channel 6 occurs when the emphysema-suffering pulmonary alveolar parenchyma is shrunk in a next step, so that the emphysema-suffering pulmonary alveolar parenchyma 3 can be readily shrunk in an efficient and rapid manner.

It will be noted that if necessary, the procedures of the injection and removal by suction of the respiratory region volume inhibitor 4 may be repeated. This enables a stronger coating film 5 to be more reliably formed over the entire inner wall surface of the emphysema-suffering pulmonary alveolar parenchyma. The formation of such a coating film contributes to reliable recovery of the elasticity of the emphysema-suffering pulmonary alveolar parenchyma and thus, lung hyperinflation can be more alleviated and suppressed. If a collateral channel exists, this collateral channel can be reliably blocked. In addition, when the above step is repeated, the thickness of the coating film can be simply controlled. Moreover, if necessary, air may be further injected after the removal by suction of an excess solution. There may be some cases where the emphysema-suffering pulmonary alveolar parenchyma is shrunk by the removal by suction of the excess solution, so that the smoothness of the inner walls cannot be secured, resulting in unsatisfactory adhesion between the coating film and the inner walls. However, when air is injected as mentioned above, the emphysema-suffering pulmonary alveolar parenchyma is inflated to provide smooth inner walls, thereby improving the adhesion between the coating film and the inner walls.

The introducing amount of the respiratory region volume inhibitor into the emphysema-suffering pulmonary alveolar parenchyma may be one sufficient to fill the emphysema-suffering pulmonary alveolar parenchyma with the respiratory region volume inhibitor and thus, no specific limitation is placed thereon. For instance, if a rise in injection pressure of the respiratory region volume inhibitor is detected, it is only necessary to stop the injection of the respiratory region volume inhibitor. Likewise, an amount of excess respiratory region volume inhibitor by suction removal after the introduction of the respiratory region volume inhibitor may be one sufficient to enable substantial removal of the respiratory region volume inhibitor from within the emphysema-suffering pulmonary alveolar parenchyma and is not critical. For example, if the respiratory region volume inhibitor cannot be suctioned, it is only necessary to stop the suction of the respiratory region volume inhibitor. It will be noted that the introduction or removal of the respiratory region volume inhibitor may be performed through the same lumen or different lumens of the catheter. In view of the ease in operation, the same lumen is preferably used.

The retention time of the respiratory region volume inhibitor within the emphysema-suffering pulmonary alveolar parenchyma is not critical and is preferably at one to five minutes. Such a time is sufficient to initiate curing of the respiratory region volume inhibitor on the inner walls of the emphysema-suffering pulmonary alveolar parenchyma thereby forming a coating film.

As stated above, the emphysema-suffering pulmonary alveolar parenchyma becomes a closed system except for a communication port with the bronchus or bronchiole. When the respiratory region volume inhibitor serving as a respiratory region volume inhibitor is removed by suction, the respiratory region volume inhibitor is removed integrally, to some extent, with the inner cavity of the emphysema-suffering pulmonary alveolar parenchyma 3. This allows the pulmonary alveolar parenchyma 3 to be shrunk in association with the suction removal.

2-2. Step (b-2)

Figure 3A:
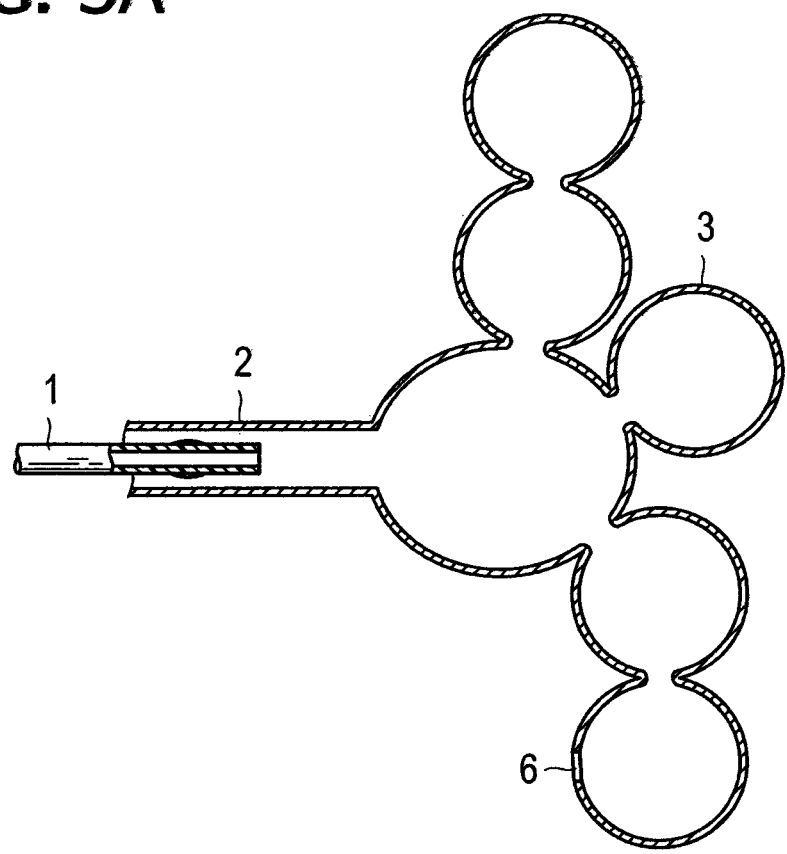
FIG. 3A is a schematic sectional view showing a step in sequence according to a second preferred embodiment of the method of the invention.
Figure 3B:
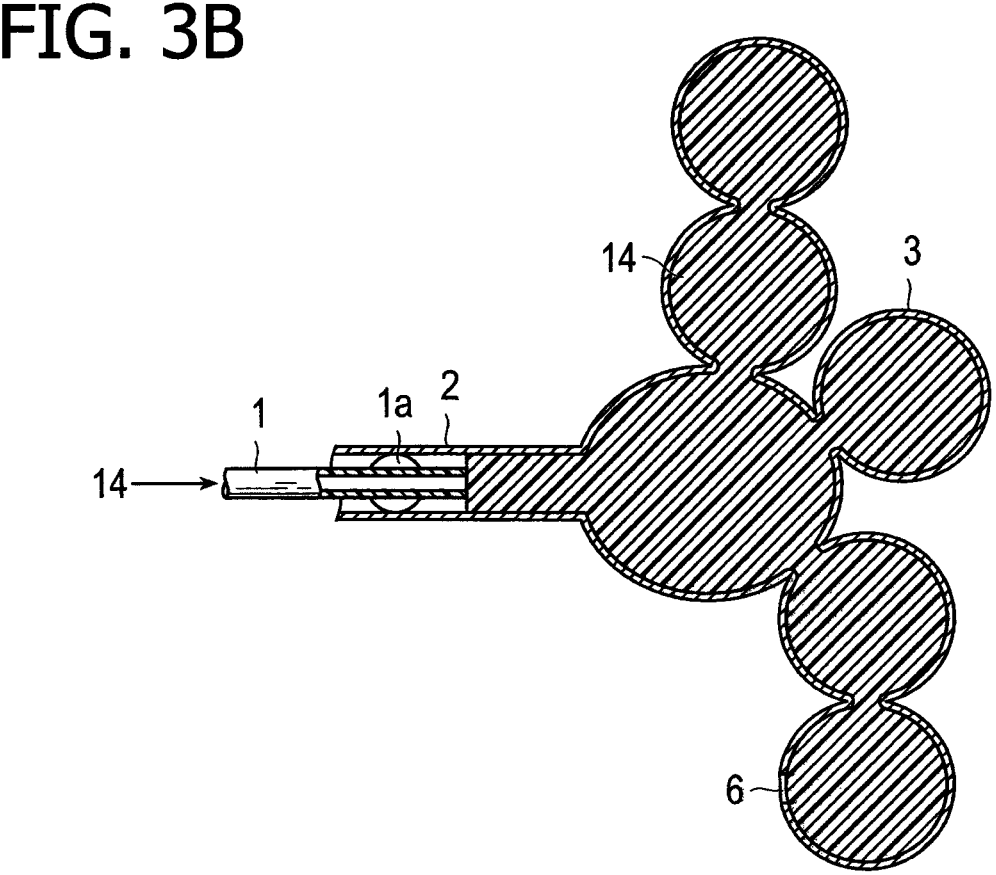
FIG. 3B is a schematic sectional view showing a step in sequence according to the second preferred embodiment of the method of the invention.

In this step, as shown in FIGS. 3B and C, a material 14 capable of being cured by reaction with water or divalent metal ions and serving as a respiratory region volume inhibitor is injected into a respiratory region 2 (FIG. 3B) via a catheter 1, followed by reaction with water or divalent metal ions (e.g. calcium ions) 15 present on the inner wall surface of a respiratory region (i.e. an emphysema-suffering pulmonary alveolar parenchyma in the FIG. 3. It will be noted that when the material 14 is injected, it is preferred to inflate a balloon 1a and seal between the catheter 1 and the inner wall of a bronchus or bronchiole 2 (FIG. 3C). This ensures reliable injection of the material 14 in the respiratory region (the emphysema-suffering pulmonary alveolar parenchyma in the FIG. 3 without flowing backward. According to the above reaction, curing of the material 14 initiates thereby forming a coating film 16 on the surface of the emphysema-suffering pulmonary alveolar parenchyma 3 (FIG. 3C). The material 14, which does not contact water or divalent metal ions 15 present on the surface of the emphysema-suffering pulmonary alveolar parenchyma 3, remains unreacted (uncured) as it is (see a partially enlarged view in FIG. 3C). Accordingly, when the material 14 is suctioned in a subsequent step (c), the unreacted (uncured) material 14 can be immediately removed, leaving the coating film 16 after the removal (FIG. 3D). It should be noted that for the suction removal of the material 14, it is preferred to inflate the balloon 1a and seal between the catheter 1 and the inner wall of the bronchus or bronchiole 2. This permits the material 14 to be reliably removed from the emphysema-suffering pulmonary alveolar parenchyma 3 without flowing toward the bronchial side. If a collateral channel 6 exists in the emphysema-suffering pulmonary alveolar parenchyma 3, the collateral channel is usually a small-sized pore, for which the coating film 16 is formed to cover the collateral channel 6 therewith. In this way, according to the above procedure, the emphysema-suffering pulmonary alveolar parenchyma 3 forms a closed system except for a communication port with the bronchus (FIG. 3D). Hence, when the emphysema-suffering pulmonary alveolar parenchyma 3 is shrunk in a next step, no air leakage through the collateral channel 6 occurs. Hence, the emphysema-suffering pulmonary alveolar parenchyma 3 can be readily shrunk in an efficient and rapid manner.

The material 14 capable of curing by reaction with water and serving as a respiratory region volume inhibitor may contain a plasticizer aside from a cyanoacrylate monomer. Using a plasticizer, flexibility is imparted to the resulting coating film, so that easy shrinkage of the emphysema-suffering pulmonary alveolar parenchyma (pulmonary alveoli or alveolar sac) can be performed in a next step (c).

It will be noted that the injection and suction removal operations of a solution containing divalent metal ions can be performed in a similar way as the foregoing injection and suction removal operations of the respiratory region volume inhibitor.

The introducing amount of the material 14 serving as a respiratory region volume inhibitor and capable of curing by reaction with water or divalent metal ions into the emphysema-suffering pulmonary alveolar parenchyma may be one sufficient to fill the emphysema-suffering pulmonary alveolar parenchyma with the material therein and is thus not critical. For instance, when a rise in injection pressure of the material is detected, it is only necessary to stop the injection of the material 14.

The contact time of water or divalent metal ions (e.g. calcium ions) on the inner walls of the emphysema-suffering pulmonary alveolar parenchyma with the material 14 is not critical and is preferably at 1 to 5 minutes. Such a time adequately allows the material 14 to be reacted with the water or divalent metal ions on the inner walls of the emphysema-suffering pulmonary alveolar parenchyma. On this occasion, it is preferred that simultaneously with the in vivo operation, the respiratory region volume inhibitor 14 is dropped on a slide glass, followed by dropping a water droplet in contact with the respiratory region volume inhibitor 14 to observe the state of the reaction. The water droplet is used as a simulant for water or divalent metal ions 15 present on the surface of the pulmonary alveolar parenchyma tissues. According to this operation, the state of reaction, proceeding in vivo, between the respiratory region volume inhibitor 14 and the water or divalent metal ions 15 can be easily and accurately understood, and the contact time of the respiratory region volume inhibitor 14 with the inner walls of the pulmonary alveolar parenchyma can be readily controlled. If the collateral channel 6 exists in the emphysema-suffering pulmonary alveolar parenchyma, the respiratory region volume inhibitor 14 in contact with the water or divalent metal ions 15 present on the surface of the emphysema-suffering pulmonary alveolar parenchyma forms the coating film 16, thereby closing the collateral channel 6. Because the collateral channel 6 is closed, an unreacted respiratory region volume inhibitor 14 can be suctioned efficiently.

As stated hereinabove, the emphysema-suffering pulmonary alveolar parenchyma becomes a closed system therein except for a communication port with the bronchus or bronchiole. Hence, when the respiratory region volume inhibitor 14 is removed by suction, removal is performed in a state of being integrated, to some extent, with the inner cavity of the emphysema-suffering pulmonary alveolar parenchyma 3. This is why the pulmonary alveolar parenchyma 3 can be shrunk in association with the suction removal.

2-3. Step (b-3)

Figure 3C:
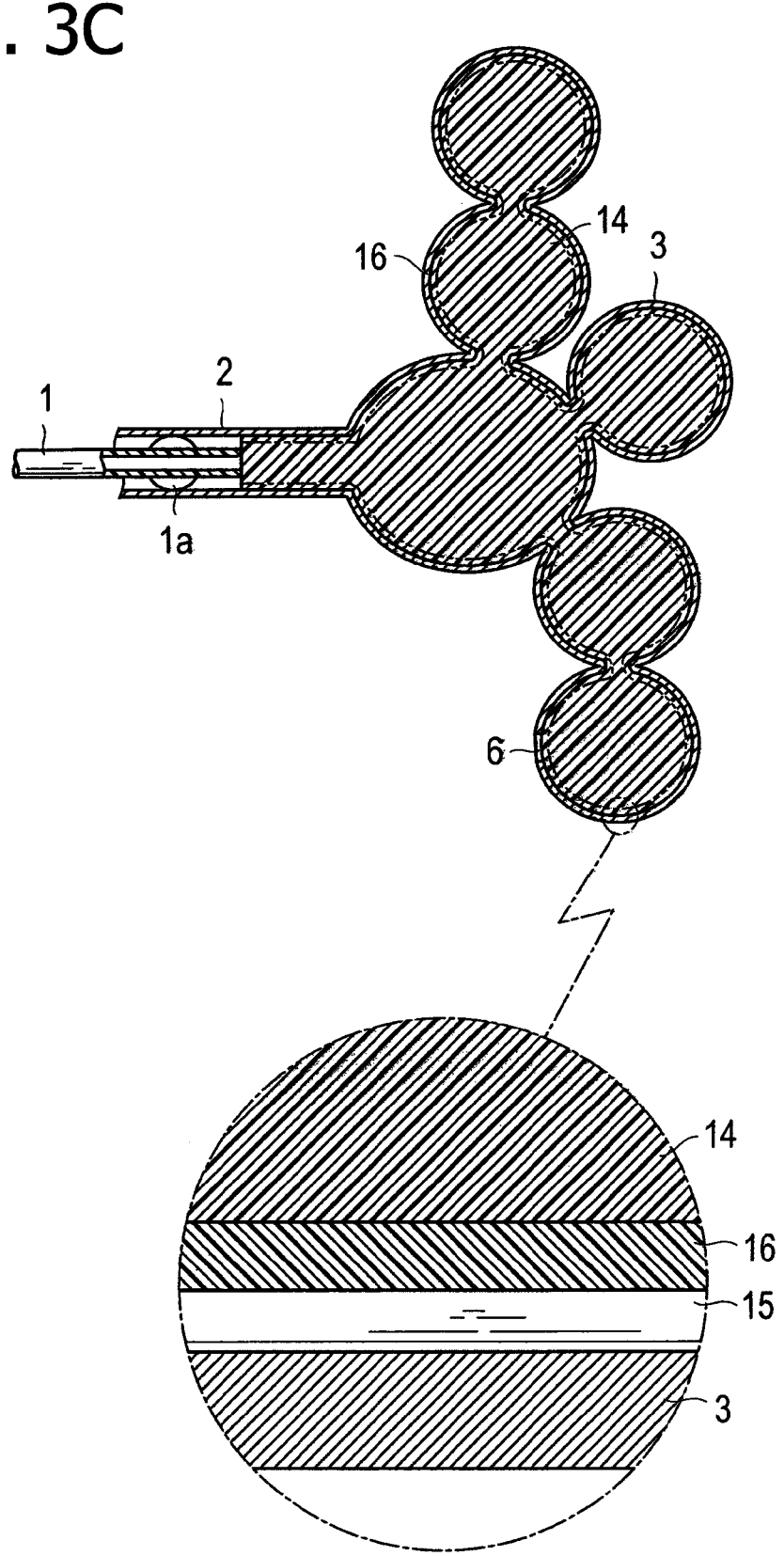
FIG. 3C is a schematic sectional view showing a step in sequence according to the second preferred embodiment of the method of the invention.
Figure 3D:
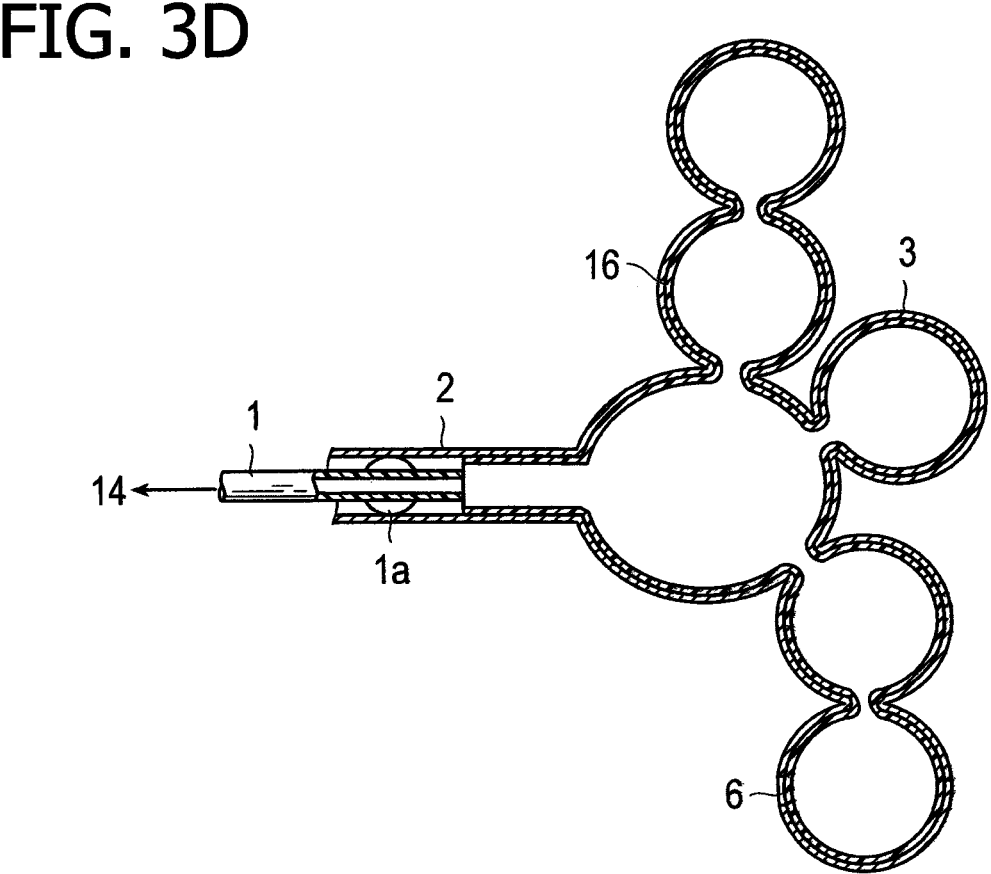
FIG. 3D is a schematic sectional view showing a step in sequence according to the second preferred embodiment of the method of the invention.
Figure 3E:
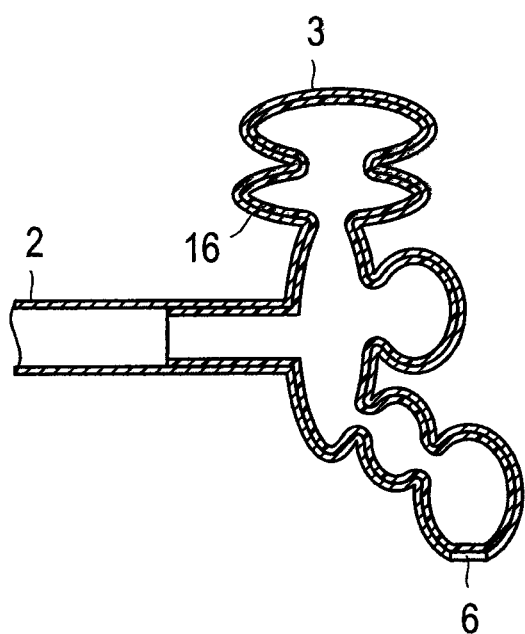
FIG. 3E is a schematic sectional view showing a step in sequence according to the second preferred embodiment of the method of the invention.
Figure 4A:
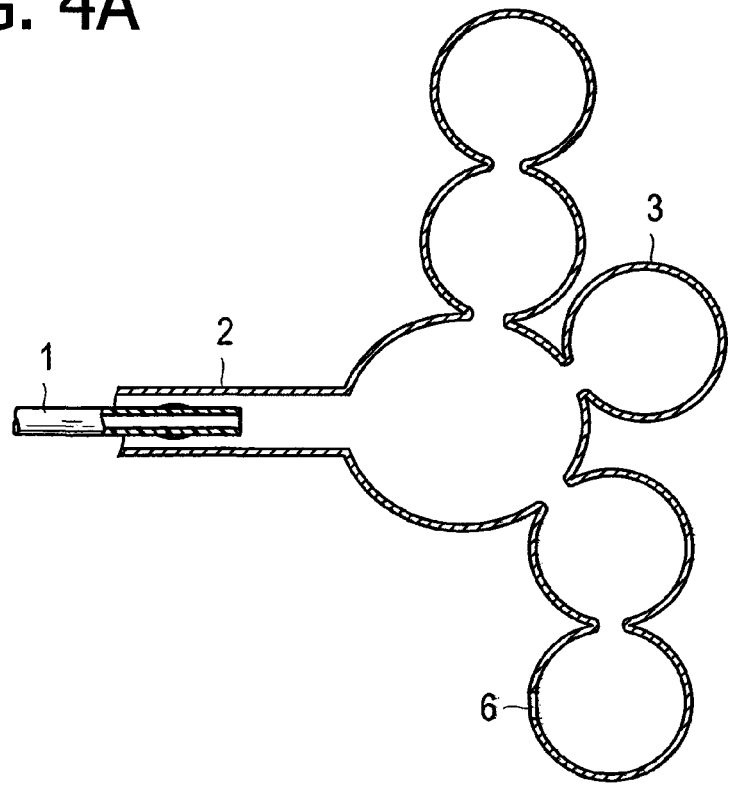
FIG. 4A is a schematic sectional view showing a step in sequence according to a third preferred embodiment of the method of the invention.
Figure 4B:
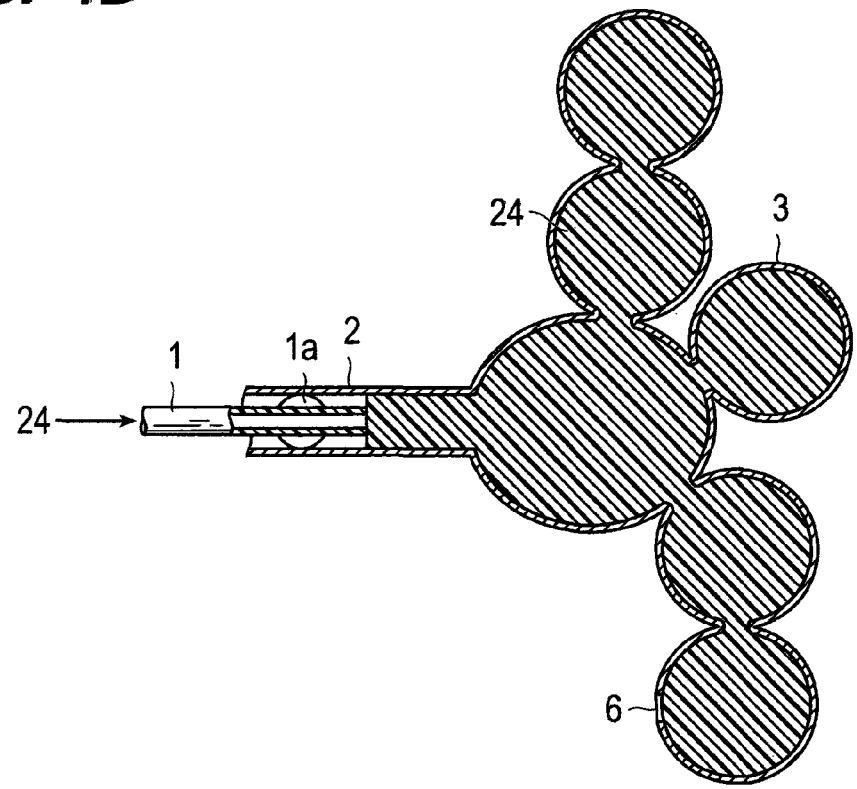
FIG. 4B is a schematic sectional view showing a step in sequence according to the third preferred embodiment of the method of the invention.
Figure 4C:
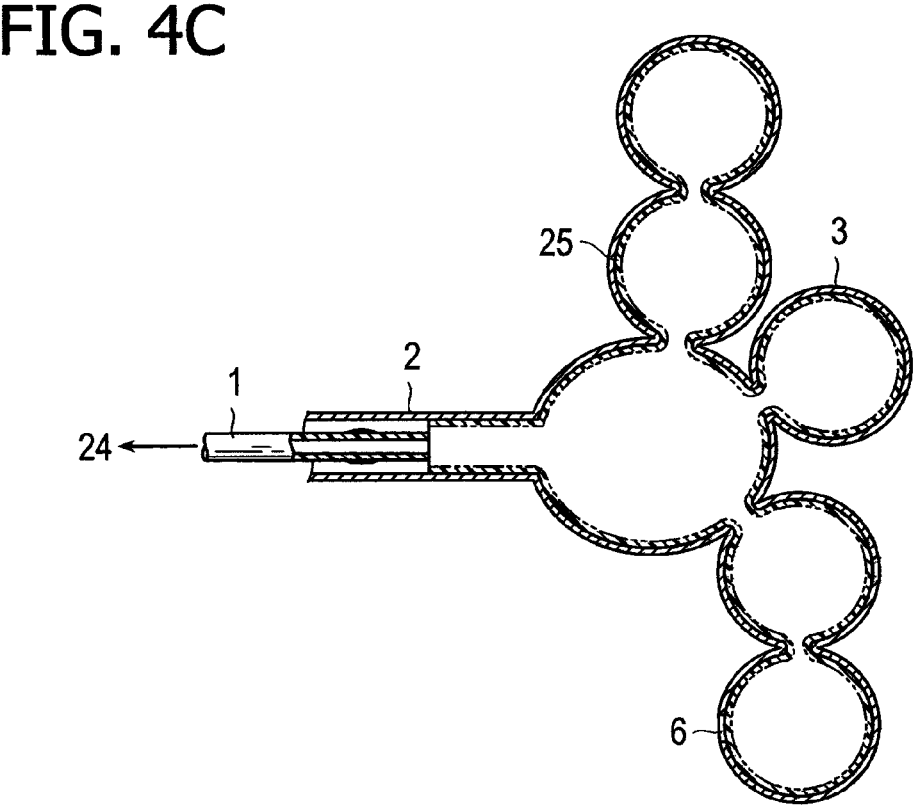
FIG. 4C is a schematic sectional view showing a step in sequence according to the third preferred embodiment of the method of the invention.

In this procedure, as shown in FIGS. 4B to E, a coating film-forming component 24 containing polymer electrolyte (A) is injected into a respiratory region 2 via a catheter 1 (FIG. 4B), after which excess polymer electrolyte (A) 24 is removed by suction (FIG. 4C). After the removal by suction, the coating film-forming component 24 containing polymer electrolyte (A) is left on the inner walls of the emphysema-suffering pulmonary alveolar parenchyma 3 to provide a thin coating film 25 (FIG. 4C). If a collateral channel 6 exists in the emphysema-suffering pulmonary alveolar parenchyma 3, the collateral channel is usually a small-sized pore and thus, the coating film 25 of the coating film-forming component 24 containing polymer electrolyte (A) is formed to cover the collateral channel 6. It will be noted that for the injection or suction removal of the coating film-forming component 24 containing polymer electrode (A), it is preferred that a balloon 1a is inflated and the catheter 1 and the inner wall of the bronchus or bronchiole 2 are sealed therebetween (FIG. 4B). This permits reliable injection of the coating film-forming component 24 containing polymer electrolyte (A) into the respiratory region (the emphysema-suffering pulmonary alveolar parenchyma in the FIG. 3 without flowing backward or reliable removal from the emphysema-suffering pulmonary alveolar parenchyma 3 without flowing out toward the bronchial side.

Figure 4D:
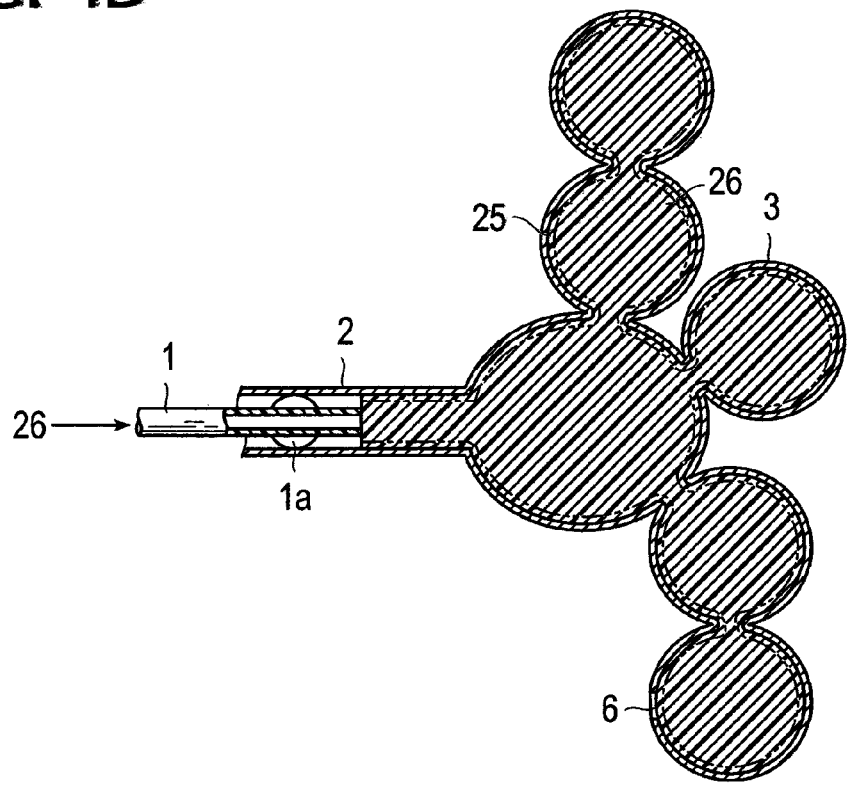
FIG. 4D is a schematic sectional view showing a step in sequence according to the third preferred embodiment of the method of the invention.
Figure 4E:
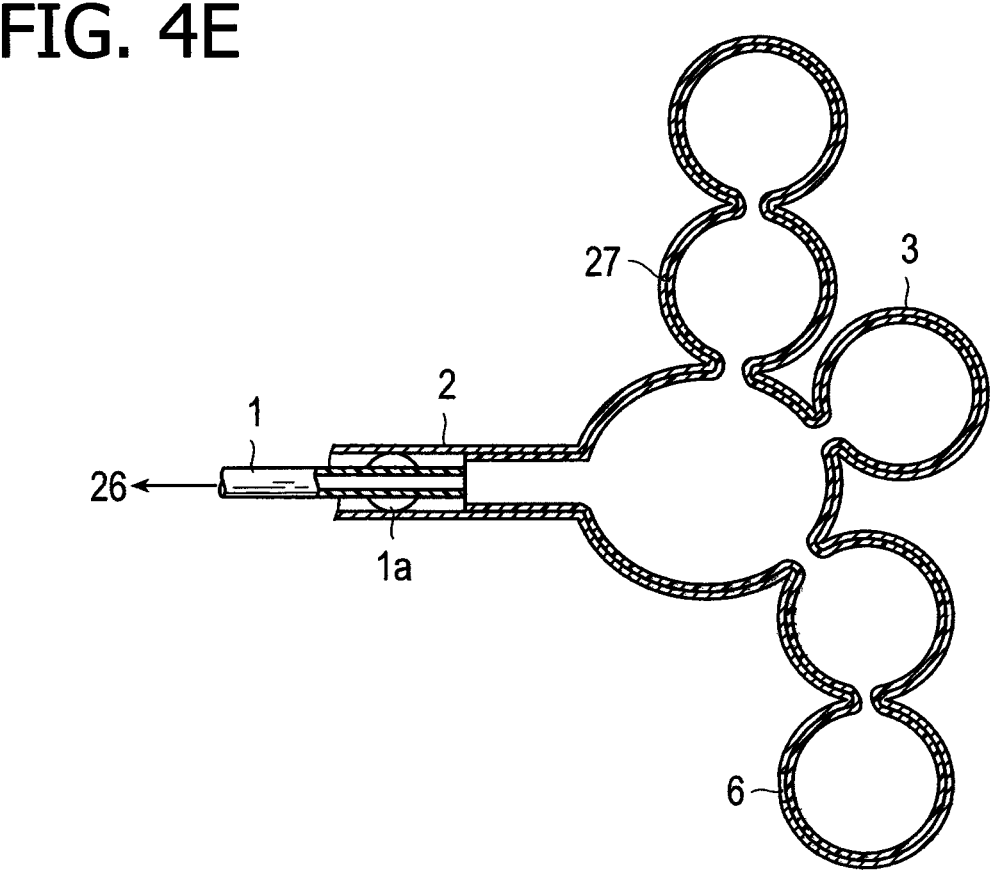
FIG. 4E is a schematic sectional view showing a step in sequence according to the third preferred embodiment of the method of the invention.

Next, an external stimulation component containing polymer electrolyte (B) having an electric charge opposite to that of polymer electrolyte (A) is injected into the respiratory region 2 via the catheter 1 to bring it into contact with the coating film 25 of polymer electrolyte (A) (FIG. 4D). The charge (e.g. a positive charge) of polymer electrolyte (B) reacts with the opposite charge (e.g. a negative charge) of polymer electrolyte (A) to form an ion complex coating film 27. In this condition, when the external stimulation component 26 containing polymer electrolyte (B) is removed by suction, the ion complex coating film 27 is left on the inner walls of the emphysema-suffering pulmonary alveolar parenchyma 3 (FIG. 4E). If a collateral channel 6 exists in the emphysema-suffering pulmonary alveolar parenchyma 3, polymer electrolyte (A) covering the collateral channel 6 as set out above reacts with polymer electrolyte (B) to form the ion complex coating film 27, so that the emphysema-suffering pulmonary alveolar parenchyma 3 forms a closed system except for a communication port with the bronchus (FIG. 4E). It will be noted that for the injection or suction removal of the external stimulation component 26 containing polymer electrolyte (B), it is preferred that the balloon 1*a* is inflated and the catheter 1 and the inner wall of the bronchus or bronchi 2 is sealed therebetween (4E). This permits the external stimulation component 26 containing polymer electrolyte (B) to be reliably injected into the respiratory region (the emphysema-suffering pulmonary alveolar parenchyma in the FIG. 3 without flowing backward or to be reliably removed from the emphysema-suffering pulmonary alveolar parenchyma 3 without flowing out toward the bronchial side.

In this step, if necessary, the injection and suction removal operations of the coating film-forming component containing polymer electrolyte (A) and the injection and suction removal operations of the external stimulation component containing polymer electrolyte (B) may be further alternately repeated. For instance, after the removal by suction of the external stimulation component 26 containing polymer electrolyte (B), the coating film-forming component containing polymer electrolyte (A) may be injected into the respiratory region via the catheter, followed by removal of excess polymer electrolyte (A) by suction (not shown). According to this operation, the electric charge (negative charge in the above instance) of polymer electrolyte (B) of the external stimulation component that does not take part in the formation of the ion complex coating film 27 reacts with the charge (positive charge in the above instance) of polymer electrolyte (A) of the coating film-forming component thus injected, thereby further forming a coating film. Thus, this operation ensures formation of a stronger coating film and the shrinkage of the emphysema-suffering pulmonary alveolar parenchyma in a next step can be performed in a more reliable and easier manner. If a collateral channel exists, this collateral channel can be reliably blocked. In addition, when the above step is repeated, the film thickness can be more easily controlled. It will be noted that in the method of the invention, polymer electrolyte (A) and polymer electrolyte (B) are used as a respiratory region volume inhibitor according to the invention.

Polymer electrolyte (A) of the coating film-forming component 24 and polymer electrolyte (B) of the external stimulation component 26 may be ones that should have mutually opposite charges. For instance, where polymer electrolyte (A) has a negative charge, polymer electrolyte (B) should have a positive charge. Similarly, where polymer electrolyte (A) has a positive charge, polymer electrolyte (B) should have a negative charge.

Where injection into the respiratory region is performed in the form of a solution or dispersion, the concentration of polymer electrolyte (A) or polymer electrolyte (B) in the solution or dispersion is not critical and is preferably at 5 to 50 mass %. When using such a concentration, the solution or dispersion is able to readily, efficiently form a coating film on the inner walls of the emphysema-suffering pulmonary alveolar parenchyma. It will be noted that the concentrations of polymer electrolyte (A) and polymer electrolyte (B) in the respective solutions or dispersions may be the same or different.

The introducing amount of polymer electrolyte (A) or polymer electrolyte (B) in the emphysema-suffering pulmonary alveolar parenchyma may be one sufficient to fill the emphysema-suffering pulmonary alveolar parenchyma therein with polymer electrolyte (A) or polymer electrolyte (B) and is not critical. For instance, when a rise in injection pressure of polymer electrolyte (A) or polymer electrolyte (B) is detected, it is only necessary to stop the injection of polymer electrolyte (A) or polymer electrolyte (B). Likewise, an amount of polymer electrolyte (A) or polymer electrolyte (B) to be removed by suction after introduction of polymer electrolyte (A) or polymer electrolyte (B) may be one sufficient to substantially remove the polymer electrolyte (A) or polymer electrolyte (B) from within the emphysema-suffering pulmonary alveolar parenchyma and is not critical. For instance, when polymer electrolyte (A) or polymer electrolyte (B) cannot be suctioned, it is only necessary to stop the suction of polymer electrolyte (A) or polymer electrolyte (B). It will be noted that the introduction and removal of polymer electrolyte (A) or polymer electrolyte (B) may be preformed via the same or different lumens of a catheter, respectively. When taking the ease in operation into account, it is preferred to use the same lumen. The introduction and removal of polymer electrolyte (A) or polymer electrolyte (B) may also be preformed via the same or different lumens of a catheter. The introduction and removal operations of the coating film-forming component 24 containing polymer electrolyte (A) and the external stimulation component 26 containing polymer electrolyte (B) may be respectively performed once and are preferably repeated several times. In doing so, the polymer electrolyte can cover the entire inner walls of the emphysema-suffering pulmonary alveolar parenchyma.

After the introduction of polymer electrolyte (A) and polymer electrolyte (B), an appropriate reactive gas may be introduced into the emphysema-suffering pulmonary alveolar parenchyma. This enables the introduced polymer electrolyte to be uniformly coated on the surface of the emphysema-suffering pulmonary alveolar parenchyma 3.

The contact time of polymer electrolyte (A) and polymer electrolyte (B) in the coating film 25 is not critical and preferably at 1 to 10 minutes. Such a time is sufficient to allow reaction between polymer electrolyte (A) and polymer electrolyte (B).

After the reaction between polymer electrolyte (A) and polymer electrolyte (B), the external stimulation component 26 containing polymer electrolyte (B) is removed by suction. At this stage, the emphysema-suffering pulmonary alveolar parenchyma becomes a closed system therein except for a communication port with the bronchus or bronchiole. Accordingly, when the external stimulation component 26 containing polymer electrolyte (B) is removed by suction, the removal is performed in a state of being integrated, to some extent, with the inner cavity of the emphysema-suffering pulmonary alveolar parenchyma 3. Hence, the pulmonary alveolar parenchyma 3 can be shrunk in association with the removal by suction.

The respiratory region volume inhibitor used in the above steps (b-1) to (b-3) is slow in coating film-forming (curing) speed. This is especially preferred in the sense that according to the steps (b-1) to (b-3), curing is completed after the shrinkage of the emphysema-suffering pulmonary alveolar parenchyma in a next step (c) thereby enabling the shrinkage to be maintained.

3. Step (c)

In this step, the emphysema-suffering pulmonary alveolar parenchyma (pulmonary alveoli or alveolar sacs), in which the coating film in the form of a balloon-shaped closed pouch on the inner walls in the above step (b) has been formed, is shrunk. According to this step, the emphysema-suffering pulmonary alveolar parenchyma should preferably be shrunk integrally with the coating film of the balloon-shaped closed pouch in a rapid manner. By this, the air retained in the emphysema-suffering pulmonary alveolar parenchyma can be efficiently removed. Especially, the respiratory region volume inhibitor used in the steps (b-1) to (b-3) is so slow in coating film-forming (curing) speed that the formation of the coating film is completed after the shrinkage. Accordingly, the shrinkage state of the emphysema-suffering pulmonary alveolar parenchyma can be maintained. This leads to an efficient reduction in volume of the pulmonary alveolar parenchyma, thereby permitting a reduced volume ascribed to breathing to be maintained. This is why lung hyperinflation, which is one of factors of debilitating an affected patient by obstruction in pulmonary emphysema or air-passage bronchus, can be alleviated or suppressed. When the emphysema-suffering pulmonary alveolar parenchyma is made smaller in size than an original one, peripheral bronchi can be suppressed or prevented from suffering compression and blockage caused by surrounding pulmonary alveolar parenchyma. In addition thereto, in the method of (a) to (c) according to the invention, treatment is carried out via a catheter without need of a surgical treatment and thus, a burden on a patient can be reduced.

In this step, although the emphysema-suffering pulmonary alveolar parenchyma is shrunk, the manner of shrinkage of the emphysema-suffering pulmonary alveolar parenchyma (pulmonary alveoli or alveolar sacs) is not specifically limited. For instance, the following methods (c-1) to (c-4) are preferably used:

(c-1) a method of filling a reactive gas via a catheter in the pulmonary alveoli or alveolar sacs, blocking the bronchus or bronchiole by a bronchus or bronchiole blocking means and injecting a gas absorbent capable of absorbing the reactive gas into the pulmonary alveoli or alveolar sacs;

(c-2) a method of performing the above step (b) using a respiratory region volume foamy inhibitor as a respiratory region volume inhibitor and after the step (b), causing the foams of the respiratory region volume inhibitor to disappear or removing the respiratory region volume foamy inhibitor by suction;

(c-3) a method of removing a residual gas left in the pulmonary alveoli or alveolar sacs by suction via a catheter; and (c-4) a method of removing the respiratory region volume inhibitor from pulmonary alveoli or alveolar sacs.

It will be noted that the above step (c-4) is overlapped with the removal by suction of the respiratory region volume inhibitor in the foregoing steps (b-1) to (b-3). Accordingly, if the respiratory region volume inhibitor is removed by suction in the steps (b-1) to (b-3), the step (c-4) can be omitted.

The preferred methods of (c-1) to (c-3) are now described in detail although the invention should not be construed as limited thereto.

3-1. Step (c-1)

Figure 2D:
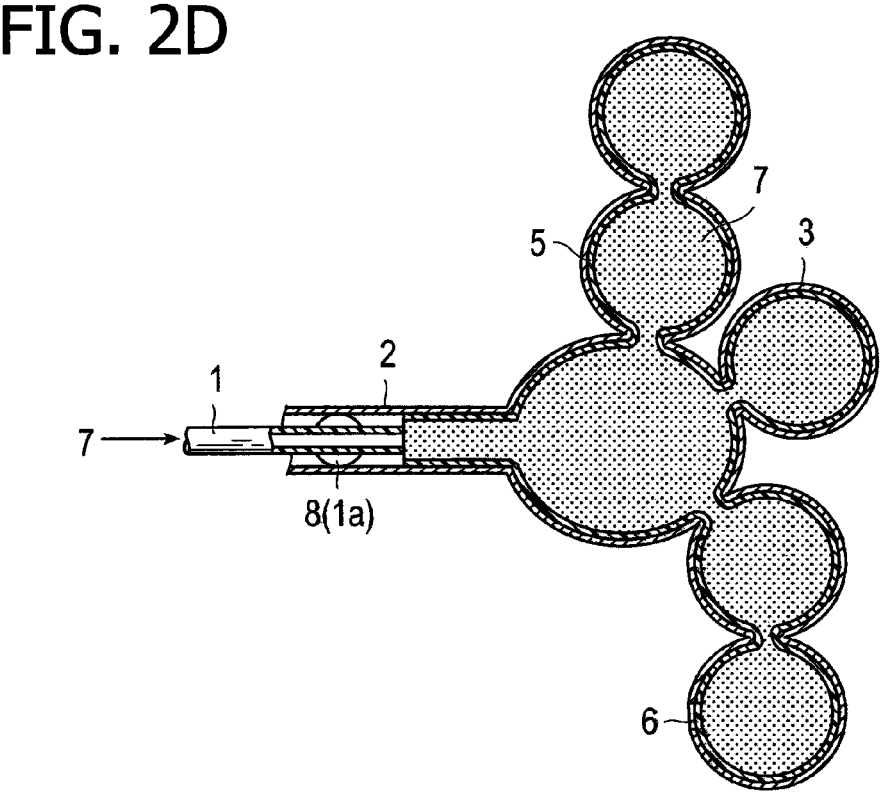
FIG. 2D is a schematic sectional view showing a step in sequence according to the first preferred embodiment of the method of the invention.
Figure 2E:
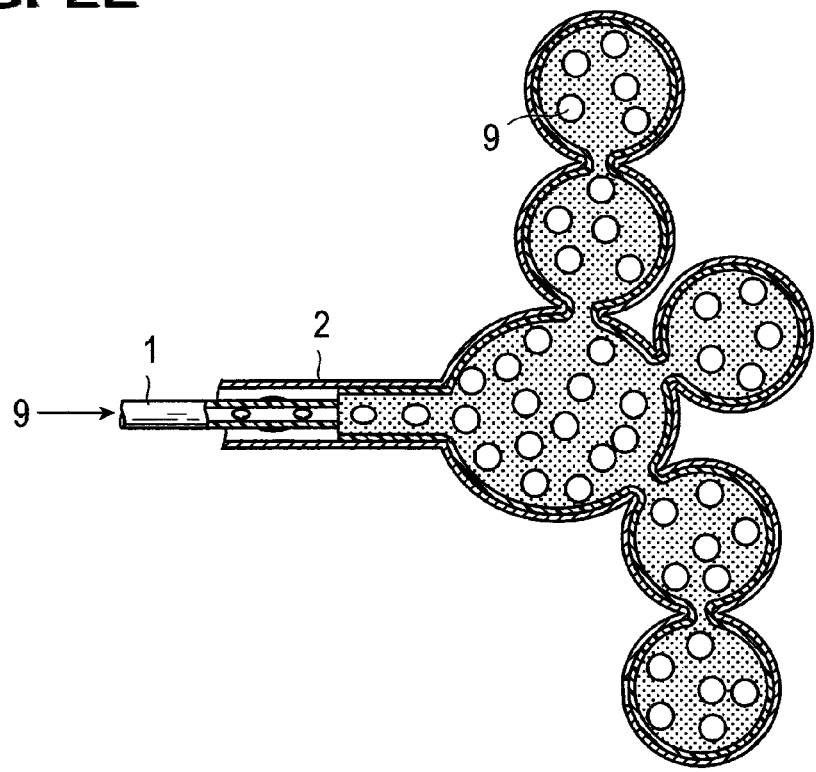
FIG. 2E is a schematic sectional view showing a step in sequence according to the first preferred embodiment of the method of the invention.
Figure 2F:
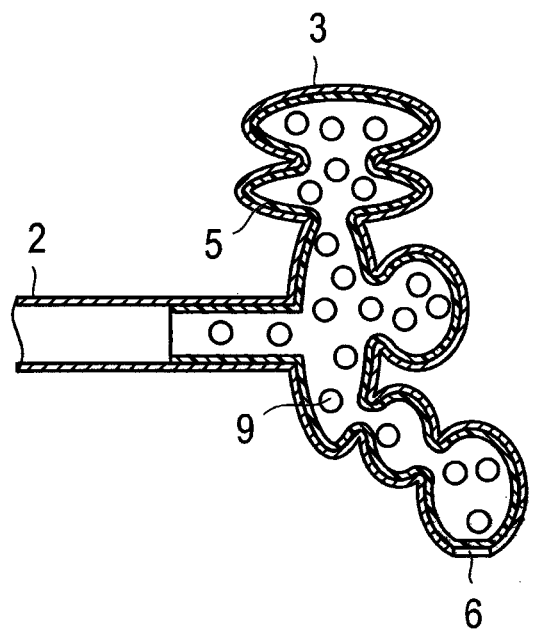
FIG. 2F is a schematic sectional view showing a step in sequence according to the first preferred embodiment of the method of the invention.

In this procedure, as shown in FIGS. 2D to F, a reactive gas 7 is injected into a respiratory region 2 via a catheter 1 to fill the reactive gas 7 in the pulmonary alveoli or alveolar sacs (emphysema-suffering pulmonary alveolar parenchyma) 3. It will be noted that when the reactive gas 7 is filled, it is preferred to inflate a balloon 1a and seal between the catheter 1 and the inner walls of the bronchus or bronchiole (FIG. 2D). This permits the reactive gas 7 to be more reliably filled. Next, the bronchus or bronchiole 2 is blocked with a bronchus or bronchiole-blocking means 8 (FIG. 2D). When the bronchus or bronchiole 2 is blocked in this way, a sufficient amount of the reactive gas 7 is introduced into the emphysema-suffering pulmonary alveolar parenchyma 3, thus permitting efficient reaction with the respiratory region volume inhibitor 3 in a coating film 5. Subsequently, a gas absorbent 9 capable of absorbing the reactive gas is injected into the pulmonary alveoli or alveolar sacs (emphysema-suffering pulmonary alveolar parenchyma) 3 (FIG. 2E). Upon absorption of the reactive gas with the gas absorbent 9, the emphysema-suffering pulmonary alveolar parenchyma coheres to reduce the lung capacity of the emphysema-suffering pulmonary alveolar parenchyma (FIG. 2F). Since the coating film 5 is formed in the foregoing step (b) so that the leakage of air in the emphysema-suffering pulmonary alveolar parenchyma is suppressed or prevented, the volume of the pulmonary alveolar parenchyma can be rapidly reduced. It will be noted that the gas absorbent 9 can be removed by suction or the like. However, the shrunk pulmonary alveolar parenchyma does not function as pulmonary alveoli or alveolar sacs, so that it is not always necessary to remove the gas absorbent 9 as shown in FIG. 2F.

The reactive gas is not critical and is preferably one that has reactivity against the respiratory region volume inhibitor 3 in the coating film in the form of the balloon-shaped closed pouch formed in the step (b). In this case, the reactive gas 7 reacts with the respiratory region volume inhibitor 3 of the coating film formed in the step (b) to initiate curing slowly, and the curing is completed after shrinkage of the emphysema-suffering pulmonary alveolar parenchyma. Thus, the reduced lung capacity of the emphysema-suffering pulmonary alveolar parenchyma can be maintained. The reactive gases used herein include oxygen, carbon dioxide and the like. These reactive gases may be used singly or in the form of a mixed gas of two or more. Of the reactive gases, oxygen is preferred. These gases are ones that originally exist in the lungs and are safe if absorbed in the body.

The introducing amount of the reactive gas into the emphysema-suffering pulmonary alveolar parenchyma may be one sufficient to fill the emphysema-suffering pulmonary alveolar parenchyma with the reactive gas and is not critical. For instance, when a rise in injection pressure of the reactive gas is detected, it is only necessary to stop the injection of the reactive gas. The introduction of the reactive gas into the emphysema-suffering pulmonary alveolar parenchyma may be performed by use of the same catheter lumen used for the introduction of the respiratory region volume inhibitor, or may be performed by a catheter lumen different from that used for the introduction of the respiratory region volume inhibitor.

The retention time of the reactive gas introduced into the emphysema-suffering pulmonary alveolar parenchyma is not specifically limited and is preferably at 1 to 10 minutes. Within such a time, the reactive gas can adequately react with the respiratory region volume inhibitor in the coating film.

The means (blocking means) 8 for blocking the bronchus or bronchiole is not specifically limited in type and may be either a transiently blocking one or a permanently blocking one. The former blocking means is not critical and may be achieved, for example, by attaching a balloon 1a to the catheter 1 as shown in FIG. 2D. It is to be noted that where the balloon 1a is inflated upon filling of the reactive gas 7, it is necessary to continue the blockage in the bronchus or bronchiole 2 in the course of filling and subsequent operations of the reactive gas 7. In the latter blocking means, no limitation is placed thereon and such blocking can be achieved by blocking the bronchus or bronchiole 2 with a soft member such as sponge or the like. In this way, the leakage of the reactive gas 7 from the emphysema-suffering pulmonary alveolar parenchyma 3 is suppressed or prevented, so that the reaction efficiency between the reactive gas 7 and the respiratory region volume inhibitor 3 can be improved. The set position of the blocking means 8 is not specifically limited. For instance, the blocking means may be set up either at a distal terminal end of the catheter or at bronchial (proximal) side from the distal terminal end of the catheter. If the tip end of the catheter is located within the bronchus, the blocking means is preferably set up at the catheter to an extent of not exceeding the branch at the proximal side of the bronchus. This can prevent the reactive gas from leaking toward the branch side at the proximal side. It will be noted that prior to the introduction of the reactive gas, the bronchus or bronchiole 2 may be preliminarily blocked. This will suppress or prevent the reactive gas from flowing backward to the bronchial (proximal) side of the bronchus or bronchiole 2 to allow the reactive gas to be efficiently introduced into a desired emphysema-suffering pulmonary alveolar parenchyma. On this occasion, although a usable blocking means for the bronchus or bronchiole is not specifically limited, such a blocking means 8 may be likewise sued, for example.

The gas absorbent 9 is not critical so far as it is able to absorb the reaction gas 7 and may be appropriately selected depending on the type of reactive gas 7. For instance, mention is made of gas absorbents containing as a main component: silica, ceramics, porous ceramics, magnesia, titania, calcium silicate and activated carbon; iron powders such as pure iron powder, cast iron powder, steel powder, reduced iron powder, atomized iron powder, sponge iron powder, electrolytic iron powder and iron alloy powders, aluminum powder, magnesium powder and silicon fine powder; L-ascorbic acid and isoascorbic acid (erythorbic acid) and alkali metal and alkaline earth metal salts thereof; polyhydric alcohols such as glycerine, ethylene glycol, propylene glycol and the like; phenolic compounds such as catechol, resorcin, hydroxynon, gallic acid, pyrogallol and tocopherol; and reducing sugars such as glucose, fructose, sorbitol, xylose and the like. These gas absorbents may be used singly or in the form of a mixture of two or more. Of the above gas absorbents, iron powders, ceramics and porous ceramics are preferred. These are excellent in safety.

When iron powder is used among the above gas absorbents, it is preferred to use an oxidation promoter. The use of an oxidation promoter can lead to an improvement in oxygen absorption function. The oxidation promoter is not critical and mention is made of alkali metal or alkaline earth metal halides such as NaCl, CaCl2, MgCl2 and the like and halides of ion exchange resins, hydrochloric acid, hypochlorites and the like. The amount of the oxidation promoter is preferably at 0.01 to 20 parts by weight per 100 parts by weight of the iron powder.

The introducing amount of the gas absorbent into the emphysema-suffering pulmonary alveolar parenchyma may be one sufficient to reduce the volume of the emphysema-suffering pulmonary alveolar parenchyma by sufficient absorption of the reactive gas and can be appropriately selected without specific limitation while taking the volume of the emphysema-suffering pulmonary alveolar parenchyma into consideration. Alternatively, when a rise in injection pressure of the gas absorbent is detected, the injection of the gas absorbent may be stopped. The introduction of the gas absorbent into the emphysema-suffering pulmonary alveolar parenchyma may be performed by use of the same catheter lumen as used for the introduction of a respiratory region volume inhibitor or reactive gas or may be performed by use of a catheter lumen different from that used for the introduction of a respiratory region volume inhibitor or reactive gas.

The retention time of the introduced gas absorbent into the emphysema-suffering pulmonary alveolar parenchyma is not critical and is preferably at 1 to 10 minutes. Such a time enables the gas absorbent to absorb the reactive gas, thereby reducing the volume of the emphysema-suffering pulmonary alveolar parenchyma.

3-2. Step (c-2)

In this method, a respiratory region volume foamy inhibitor is provided as a respiratory region volume inhibitor. Accordingly, after the step (b), when a foam gas of an uncured respiratory region volume foamy inhibitor 14 is released from the body or the foams absorbed in the body is caused to disappear, the volume of the emphysema-suffering pulmonary alveolar parenchyma 3 can be reduced. In this case, no step of FIG. 3D is used, but the steps proceed from FIG. 3C directly to FIG. 3E (FIG. 3C->FIG. 3E). The respiratory region volume foamy inhibitor can be prepared by introducing nitrogen gas, helium gas, argon gas, carbon monoxide, carbon dioxide, carbonic acid gas, oxygen or the like into the respiratory region volume inhibitor described in the foregoing step (b), particularly the material 14 capable of curing by reaction with water or divalent metal ions as described in the foregoing step (b-2), to provide a foamy product.

The foams of an uncured respiratory region volume inhibitor 14 may be caused to naturally disappear or defoaming may be promoted by use of a defoamer. It is preferred that the foams of the respiratory region volume foamy inhibitor 14 after curing are caused to naturally disappear by absorption through diffusion. The defoamers usable in the latter case are not critical and such defoamers employed in the medical field can be likewise used. More particularly, mention is made of: lower alcohols such as methanol, ethanol, isopropanol, butanol and the like; silicone compounds such as silicone oil; and organic polar compounds such as 2-ethylhexanol, diisobutyl carbinol, amyl alcohol, tributyl phosphate, sodium octyl phosphate, a metal stearate, a metal palmitate, isoamyl stearate ester, diglycol laurate ester, sorbitan trioleate ester, polyoxyethylene sorbitan monolaurate ester, a pluronic nonionic surfactant, and a polyalkylene glycol and derivatives thereof. The defoamers may be used singly or in the form of a mixture of two or more. Of the defoamers, polyalkylene glycol derivatives are preferred. These are excellent in defoamability. The introducing amount of the defoamer into the emphysema-suffering pulmonary alveolar parenchyma is not critical so far as it is sufficient to defoam an uncured respiratory region volume foamy inhibitor to a satisfactory extent of reducing the amount of the emphysema-suffering pulmonary alveolar parenchyma. The defoamer is preferably used at about 0.001 to about 5 mass % relative to the initially introduced amount of the respiratory region volume foamy inhibitor. It will be noted that the introduction of the defoamer into the emphysema-suffering pulmonary alveolar parenchyma may be performed by use of either the same catheter lumen used for the introduction of the respiratory region volume inhibitor or a catheter lumen different from that used for the introduction of the respiratory region volume inhibitor.

The volume of the emphysema-suffering pulmonary alveolar parenchyma 3 may be reduced by removing by suction an uncured respiratory region volume foamy inhibitor 14 via the catheter 1. In this case, the steps of FIG. 3C to 3E proceed via FIG. 3D (FIG. 3C->FIG. 3D->FIG. 3E). The amount of removal by suction of the respiratory region volume foamy inhibitor 14 is not critical so far as it is sufficient to substantially remove an uncured respiratory region volume foamy inhibitor from the emphysema-suffering pulmonary alveolar parenchyma. For example, if the respiratory region volume foamy inhibitor cannot be suctioned, it is only necessary to stop the suction of the respiratory region volume foamy inhibitor. The removal by suction of the respiratory region volume foamy inhibitor may be performed by the same catheter lumen used for the introduction of the respiratory region volume inhibitor or may be performed by a catheter lumen different from that used for the respiratory region volume inhibitor.

3-3. Step (c-3)

Figure 4F:
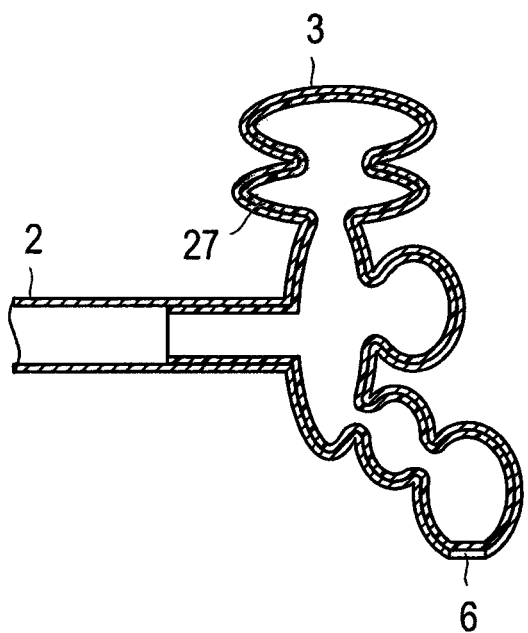
FIG. 4F is a schematic sectional view showing a step in sequence according to the third preferred embodiment of the method of the invention.

In this procedure, the residual gas in the pulmonary alveoli or alveolar sacs is removed by suction via the catheter (FIG. 4F). Even after the removal by suction of the respiratory region volume inhibitor, the emphysema-suffering pulmonary alveolar parenchyma 3 may remain inflated in some cases. In such a case, the residual gas in the emphysema-suffering pulmonary alveolar parenchyma 3 is removed by suction via the catheter, whereupon since the emphysema-suffering pulmonary alveolar parenchyma 3 is in a closed system except for a communication port with the bronchus or bronchiole 2, the volume of the emphysema-suffering pulmonary alveolar parenchyma can be reduced in volume in an efficient and rapid manner. The removal by suction of the residual gas in the emphysema-suffering pulmonary alveolar parenchyma 3 is completed at the time when the residual gas cannot be further suctioned.

3-4. Step (c-4)

In this procedure, the respiratory region volume inhibitor is removed by suction from the pulmonary alveoli or alveolar sacs. As set out hereinabove, the emphysema-suffering pulmonary alveolar parenchyma is becomes a closed system except for a communication port with the bronchus or bronchiole. Accordingly, the pulmonary alveolar parenchyma 3 can be shrunk in association with the removal by suction of the respiratory region volume inhibitor. This procedure is preferred for its very simplicity. It will be noted that if the pulmonary alveolar parenchyma 3 cannot be well shrunk even after the performance of this operation, it is preferred to carry out at least one of the steps (c-1) to (c-3).

In the foregoing, although the step (a), steps (b-1) to (b-3) and steps (c-1) to (c-3) have been described in detail, the combinations of these steps are not specifically limited and any combinations may be used. Preferably, mention is made of combinations of: steps (a) and (b-1); steps (a) and (b-2); steps (a) and (b-3); steps (a), (b-1) and (c-1); steps (a), (b-1) and (c-3); steps (a), (b-2) and (c-2); and steps (a), (b-3) and (c-3). Of these, combinations of: steps (a) and (b-1); steps (a) and (b-2); steps (a) and (b-3); steps (a), (b-1) and (c-1); steps (a), (b-2) and (c-2); and steps (a), (b-3) and (c-3) are more preferred.

As stated hereinbefore, according to the method of the invention, air retained in the emphysema-suffering pulmonary alveolar parenchyma can be efficiently removed and the reduced volume can be maintained. Thus, lung hyperinflation, which is one of factors of debilitating an affected patient by obstruction in pulmonary emphysema or air-passage bronchus, can be alleviated and suppressed. When the size of the emphysema-suffering pulmonary alveolar parenchyma is made smaller than an original one, the compression or obstruction of the peripheral bronchi with surrounding pulmonary alveolar parenchymas can be alleviated or suppressed. The treating method of the invention is performed via a catheter and no surgical treatment is needed, so that a burden on a patient can be mitigated.

Additionally, according to the invention, since the elasticity of the emphysema-suffering pulmonary alveolar parenchyma is recovered by forming a coating film on the inner walls of the emphysema-suffering pulmonary alveolar parenchyma, lung hyperinflation can be alleviated or suppressed.

Further, according to the invention, the coating film can be formed on cysts that may lead to pneumothorax, thereby reducing the volume. In this case, a metal needle may be percutaneously punctured into the cyst portion, or a catheter may be inserted into the cyst portion via a bronchus (transbrochially), so that retained air can be efficiently removed in a similar way as in the foregoing steps and examples, or the reduced volume can be maintained.

Furthermore, the coating film can be formed on a damaged area of the pleura that leads to pneumothorax so as to reduce and keep the volume of the pneumothorax. In this case, a metal needle is percutaneously punctured into the cyst portion or a catheter is inserted into the pneumothorax portion via a bronchus (transbrochially) to efficiently remove the retained air in the same manner as in the foregoing step and examples, or the reduced volume can be maintained.

EXAMPLES

The method of transbrochially coating tissues of alveolar sacs (air sacs) or pulmonary alveoli, tissues of terminal bronchioles and tissues of collateral pathways at an arbitrary portion thereof is illustrated in detail based on preferred examples. In this regard, however, the technical range of the invention should not be construed as limited to the following examples alone.

Example 1

1 g of gelatin (made by Wako Pure Chemical Industries, Ltd.) was added to 5 cc of hot water of 60° C. and mixed together to prepare a respiratory region volume inhibitor according to the invention.

As shown in FIG. 2A, an OTW PTCA balloon catheter 1 [Ryujin Plus OTW (registered trade name), Medical Device Approval Number: 21600BZZ00035, made by Terumo Corporation] used for the stenotic treatment of the inner cavity of blood vessel in the cardiovascular region was inserted into the inner cavity of a bronchiole 2 from a working lumen (not shown) of a bronchoscope. A guide wire [Runthrough (registered trade name), made by Terumo Corporation] (outer diameter: 0.014 inches) was preliminarily inserted into the working lumen of the bronchoscope. The tip end of the guide wire was moved forward closely to a desired emphysema-suffering pulmonary alveolar parenchyma 3 under radioscopy. Next, the catheter was moved forward closely to the desired emphysema-suffering pulmonary alveolar parenchyma 3 under radioscopy via the guide wire, after which the guide wire was removed.

Next, as shown in FIG. 2B, a 2 wt % gelatin aqueous solution 4 was filled in a syringe as the respiratory region volume inhibitor. Using the syringe connected to a lumen for inflation of the balloon portion provided at a base end portion of the catheter 1, a balloon 1a was inflated with air to block the bronchiole 2. The gelatin aqueous solution was injected into the inner cavity of the emphysema-suffering pulmonary alveolar parenchyma 3 from the syringe via the lumen of the catheter 1. When the injection pressure of the syringe rose, the injection of the gelatin aqueous solution was stopped. In this way, a sufficient amount of the gelatin aqueous solution was injected into the inner cavity of the pulmonary alveolar parenchyma 3. The gelatin aqueous solution was allowed to stand for five minutes after the injection to initiate curing of the gelatin. Next, the gelatin aqueous solution 4 was removed by suction. A collateral channel 6 was closed by means of a coating film 5 of the gelatin formed on the inner walls of the emphysema-suffering pulmonary alveolar parenchyma 3, so that the unreacted gelatin solution 4 could be efficiently removed by suction (FIG. 2C).

As shown in FIG. 2D, the balloon 1a of the catheter 1 was inflated with air in the same way as set out above to block the bronchiole 2 and oxygen was injected as a reactive gas 7 from an inflation lumen. Since the inner cavity of the pulmonary alveolar parenchyma 3 was covered with the respiratory region volume inhibitor 4, the reactive gas 7 could be efficiently filled in the pulmonary alveolar parenchyma 3.

A shown in FIG. 2E, an iron powder serving as a gas absorbent 9 was sprayed into the inner cavity of the emphysema-suffering pulmonary alveolar parenchyma 3 via a gas-feedable lumen of the catheter 1. The introducing amount of the iron powder was about 3.2 mg per ml of the inner cavity volume of the pulmonary alveolar parenchyma 3. The sprayed iron powder absorbed the gas left in the emphysema-suffering pulmonary alveolar parenchyma 3, so that the emphysema-suffering pulmonary alveolar parenchyma 3 underwent shrinkage, and its volume was reduced (FIG. 2F). As a result of permitting the curing of the gelatin in such a state of reduced volume to further proceed, the emphysema-suffering pulmonary alveolar parenchyma 3 was held in the state of reduced volume (FIG. 2F).

Example 2

1 g of sodium hydrogen carbonate (made by Wako Pure Chemical Industries, Ltd.) and 1 g of citric acid (made by Wako Pure Chemical Industries, Ltd.), both in the form of powder, were dispersed in 5 g of ethyl-2-cyanoacrylate (commercial name of "Aron Alpha 201," made by Toagosei Co., Ltd.), to which 1 g of polyethylene glycol (made by NOF Corporation) (Mw=10000) for use as a coating film adjuster for lowering viscosity was added and mixed together at 20° C. to prepare a respiratory region volume inhibitor 14 according to the invention.

As shown in FIG. 3A, an OTW PTCA balloon catheter 1 [Ryujin Plus OTW (registered trade name), Medical Device Approval Number: 21600BZZ00035, made by Terumo Corporation] used for the stenotic treatment of the inner cavity of blood vessel in the cardiovascular region was inserted into the inner cavity of a bronchiole 2 from a working lumen (not shown) of a bronchoscope. A guide wire [Runthrough (registered trade name), made by Terumo Corporation] (outer diameter: 0.014 inches) was preliminarily inserted into the working lumen of the bronchoscope. The tip end of the guide wire was moved forward closely to a desired emphysema-suffering pulmonary alveolar parenchyma 3 under radioscopy. Next, the catheter was moved forward closely to the desired emphysema-suffering pulmonary alveolar parenchyma 3 under radioscopy via the guide wire, after which the guide wire was removed.

As shown in FIG. 3B, the respiratory region volume foamy inhibitor 14 prepared above was filled in a syringe. Using an indeflator connected to a lumen for balloon portion inflation provided at a base end portion of the catheter 1, a balloon 1a was inflated with air to block the bronchiole 2. The respiratory region volume inhibitor was injected into the inner cavity of the emphysema-suffering pulmonary alveolar parenchyma 3 from the syringe via the lumen of the catheter 1. When the injection pressure of the syringe rose, the injection of the respiratory region volume inhibitor was stopped. When a sufficient amount of the respiratory region volume inhibitor was injected into the inner cavity of the pulmonary alveolar parenchyma 3 in this way, the ethyl α-cyanoacrylate used as the component of the respiratory region volume inhibitor reacted with moisture, serving as an external stimulation 15, present on the surface of the emphysema-suffering pulmonary alveolar parenchyma 3 and rapidly cured thereby forming a coating film 16 on the inner walls of the pulmonary alveolar parenchyma 3 (FIG. 3C). At the same time, carbonic acid gas was generated to form bubbles.

Simultaneously with the commencement of the injection of the respiratory region volume inhibitor, a water droplet was dropped on the respiratory region volume inhibitor preliminarily dropped on a slide glass to observe the state of reaction between ethyl α-cyanoacrylate used as a component of the respiratory region volume inhibitor and moisture 15 present on the surface of the emphysema-suffering pulmonary alveolar parenchyma 3. After confirmation that the coating film was well formed, the respiratory region volume inhibitor was removed by suction (FIG. 3D). Since a collateral channel 6 was closed by the formation of the coating film, the respiratory region volume inhibitor containing unreacted ethyl α-cyanoacrylate could be efficiently removed by suction.

It could be confirmed that in association with the removal by suction of the ethyl α-cyanoacrylate and the defoaming of carbon dioxide introduced into the ethyl α-cyanoacrylate, the volume of the emphysema-suffering pulmonary alveolar parenchyma 3 was reduced. As a result of further progress of the curing of the ethyl α-cyanoacrylate in a reduced state of volume, the emphysema-suffering pulmonary alveolar parenchyma 3 was kept reduced in volume (FIG. 3E).

Example 3

5 g of alginic acid (made by Wako Pure Chemical Industries, Ltd., Mw=200000) was added to and mixed with water with a pH of 6 to 8 at 40° C. to prepare an alginic acid aqueous solution, followed by further dissolving 4.2 g of sodium hydrogen carbonate (made by Wako Pure Chemical Industries, Ltd.) to the aqueous solution and mixing with diluted hydrochloride acid (made by Wako Pure Chemical Industries, Ltd.) to prepare a respiratory region volume foamy inhibitor (a 10 wt % alginic acid aqueous solution introduced with carbon dioxide) according to the invention. As shown in FIG. 3A, an OTW PTCA balloon catheter 1 [Ryujin Plus OTW (registered trade name), Medical Device Approval Number: 21600BZZ00035, made by Terumo Corporation] used for the stenotic treatment of the inner cavity of blood vessel in the cardiovascular region was inserted into the inner cavity of a bronchiole 2 from a working lumen (not shown) of a bronchoscope. A guide wire [Runthrough (registered trade name), made by Terumo Corporation] (outer diameter: 0.014 inches) was preliminarily inserted into the working lumen of the bronchoscope. The tip end of the guide wire was moved forward closely to a desired emphysema-suffering pulmonary alveolar parenchyma 3 under radioscopy. Next, the catheter was moved forward closely to the desired emphysema-suffering pulmonary alveolar parenchyma 3 under radioscopy via the guide wire, after which the guide wire was removed.

As shown in FIG. 3B, the respiratory region volume foamy inhibitor 14 was filled in a syringe. Using an indeflator connected to a lumen for balloon portion inflation provided at a base end portion of the catheter 1, a balloon 1a was inflated with air to block the bronchiole 2. The respiratory region volume foamy inhibitor 14 was injected into the inner cavity of the emphysema-suffering pulmonary alveolar parenchyma 3 from the syringe via the lumen of the catheter 1. When the injection pressure of the syringe rose, the injection of the respiratory region volume foamy inhibitor 14 was stopped. When a sufficient amount of the respiratory region volume foamy inhibitor 14 was injected into the inner cavity of the pulmonary alveolar parenchyma 3 in this way, the alginic acid of the respiratory region volume foamy inhibitor 14 reacted with calcium ions 15 present on the surface of the emphysema-suffering pulmonary alveolar parenchyma 3 and rapidly cured thereby forming a coating film 16 on the inner walls of the pulmonary alveolar parenchyma 3 (FIG. 3C).

The respiratory region volume foamy inhibitor 14 was allowed to stand for three minutes after its injection to form a coating film, followed by removing the respiratory region volume foamy inhibitor 14 by suction (FIG. 3D). Since a collateral channel 6 was closed by the formation of the coating film, the respiratory region volume foamy inhibitor 14 containing unreacted alginic acid could be efficiently removed by suction.

It could be confirmed that in association with the removal by suction of the respiratory region volume foamy inhibitor 14 and the defoaming of carbon dioxide introduced into the alginic acid aqueous solution, the volume of the emphysema-suffering pulmonary alveolar parenchyma 3 was reduced. When excess respiratory region volume foamy inhibitor was removed by suction, the calcium concentration on the surface 15 of the tissues of the emphysema-suffering pulmonary alveolar parenchyma 3 became high. Hence, the reaction between the alginic acid of the respiratory region volume inhibitor 14 and the calcium ions 15 present on the surface of the emphysema-suffering pulmonary alveolar parenchyma 3 proceeded more efficiently on the tissue surface 15 of the emphysema-suffering pulmonary alveolar parenchyma 3 thereby performing coating film formation. As s consequence, the emphysema-suffering pulmonary alveolar parenchyma 3 was maintained in a state of its volume being reduced (FIG. 3E).

Example 4

There were provided 1 g of hyaluronic acid (made by Seikagaku Corporation) used as a coating film-forming component 24 containing polymer electrolyte (A) and poly (N,N-dimethylaminopropylacrylamide) (weight average molecular weight=10,000 to 500,000) used as an external stimulation component 26 containing polymer electrolyte (B). As shown in FIG. 4A, an OTW PTCA balloon catheter 1 [Ryujin Plus OTW (registered trade name), Medical Device Approval Number: 21600BZZ00035, made by Terumo Corporation] used for the stenotic treatment of the inner cavity of blood vessel in the cardiovascular region was inserted into the inner cavity of a bronchiole 2 from a working lumen (not shown) of a bronchoscope. A guide wire [Runthrough (registered trade name), made by Terumo Corporation] (outer diameter: 0.014 inches) was preliminarily inserted into the working lumen of the bronchoscope. The tip end of the guide wire was moved forward closely to a desired emphysema-suffering pulmonary alveolar parenchyma 3 under radioscopy. Next, the catheter was moved forward closely to the desired emphysema-suffering pulmonary alveolar parenchyma 3 under radioscopy via the guide wire, after which the guide wire was removed.

As shown in FIG. 4B, hyaluronic acid was filled in a syringe as polymer electrolyte (A) that is an example of the coating film-forming component 24. Using an indeflator connected to a lumen for balloon portion inflation and located at a base end portion of the catheter 1, a balloon 1a was inflated with air to block the bronchiole 2. The hyaluronic acid was injected into the inner cavity of the emphysema-suffering pulmonary alveolar parenchyma 3 from the syringe via the lumen of the catheter 1. When the injection pressure of the syringe rose, the injection of the hyaluronic acid was stopped. Next, excess hyaluronic acid was removed by suction. The injection and removal by suction of hyaluronic acid was repeated several times. Subsequently, the balloon 1a blocking the bronchiole 2 was deflated for communication with outside. At this time, a coating film 25 made of the hyaluronic acid serving as polymer electrolyte (A) 24 was formed on the tissue surface of the emphysema-suffering pulmonary alveolar parenchyma 3 (FIG. 4C).

Next, as shown in FIG. 4D, using the indeflator connected to a lumen for balloon portion inflation and provided at a base end portion of the catheter 1, the balloon 1a was again inflated with air to block the bronchiole 2. Poly(N,N-dimethylaminopropylacrylamide) (weight average molecular weight=10,000 to 500,000) serving as polymer electrolyte (B) 26 was filled in another syringe. This poly(N,N-dimethylaminopropylacrylamide) was injected into the inner cavity of the emphysema-suffering pulmonary alveolar parenchyma 3 from the syringe via a lumen of the catheter 1 different from that used for injecting hyaluronic acid. When the injection pressure of the syringe rose, the injection of the poly(N,N-dimethylaminopropylacrylamide) was stopped. When the poly(N,N-dimethylaminopropylacrylamide) was injected into the inner cavity of the emphysema-suffering pulmonary alveolar parenchyma 3 in this way, the poly(N,N-dimethylaminopropylacrylamide) started to be cured by reaction quick reaction with the hyaluronic acid constituting the coating film 25 formed on the tissue surface of the emphysema-suffering pulmonary alveolar parenchyma 3 (FIG. 4D).

After allowing to stand for five minutes after the injection of the poly(N,N-dimethylaminopropylacrylamide) to form an ion complex coating film 27 by sufficient reaction with the hyaluronic acid, excess poly(N,N-dimethylaminopropylacrylamide) was removed by suction. Thereafter, air whose viscosity was lower than hyaluronic acid and poly(N,N-dimethylaminopropylacrylamide) was injected from the tip end of the catheter 1 to uniformly cover polymer electrolyte (B) over the surface of the emphysema-suffering pulmonary alveolar parenchyma 3 (FIG. 4E).

Thereafter, the air was suctioned from the emphysema-suffering pulmonary alveolar parenchyma 3 via the catheter 1 to reduce the volume of the emphysema-suffering pulmonary alveolar parenchyma 3. The reaction between the hyaluronic acid and the poly(N,N-dimethylaminopropylacrylamide) the crosslinkage reaction proceeded in the ion complex film with a lapse of time, so that the reduced volume of the emphysema-suffering pulmonary alveolar parenchyma 3 was kept over a long time (FIG. 4F).

EXPLANATION OF REFERENCE NUMERALS

1 Catheter
2 Bronchiole
3 Pulmonary alveolar parenchyma
4 Respiratory region volume inhibitor
5 Coating film
6 Collateral channel
7 Reactive gas
14 Respiratory region volume foamy inhibitor
16 Coating film
27 Ion complex coating film

The invention claimed is:

1. A non-surgical method of reducing lung volume in a patient suffering from pulmonary emphysema comprising:
inserting a catheter into a respiratory region of the patient; the respiratory region having pulmonary alveoli or alveolar sacs, and the respiratory region including an inner wall possessing an inner peripheral surface;
injecting a respiratory region volume reducer, which comprises a coating film-forming component that contains a polymer electrolyte A having a negative charge, into the respiratory region by way of the catheter to form a coating film of the respiratory region volume reducer on the inner wall of the respiratory region; wherein polymer electrolyte A is selected from the group consisting of polyamino acids, artificially synthesized polypeptides, polysaccharides, hyaluronic acid, chondroitin, pectin, agarose, glycosaminoglycan, cellulose, starch, artificially synthesized polysaccharides, and mixtures thereof;
externally stimulating the coating film by applying polymer electrolyte B having a positive charge to form a cured balloon-shaped closed pouch made of the coating film that is in intimate contact with the inner peripheral surface of the respiratory region; wherein polymer electrolyte B is poly(N,N-dimethylaminophropylacrylamide); and
shrinking the balloon-shaped closed pouch by reducing pressure inside the balloon-shaped closed pouch from outside of the respiratory region.

2. The method of claim 1, wherein the coating film-forming component is administered to the respiratory region in an amount of 0.004 g to 200 g per application.

3. The method of claim 1, wherein the coating film-forming component comprises a foaming agent.

4. The method of claim 1, wherein the balloon-shaped closed pouch is shrunk by:
removing residual gas in the respiratory region by suction; or
removing respiratory region volume reducer from the pulmonary alveoli or the alveolar sacs.

5. The method of claim 1, wherein the polymer electrolyte A is hyaluronic acid.

6. A non-surgical method of reducing lung volume in a patient suffering from pulmonary emphysema comprising:
inserting a catheter into a respiratory region of the patient; the respiratory region having pulmonary alveoli or alveolar sacs, and the respiratory region including an inner wall possessing an inner peripheral surface;
injecting a respiratory region volume reduce, which comprises a coating film-forming component that contains a polymer electrolyte B having a positive charge, into the respiratory region by way of the catheter to form a coating film of the respiratory region volume reducer on the inner wall of the respiratory region; wherein polymer electrolyte B is poly(N,N-dimethylaminopropylacrylamide);
externally stimulating the coating film by applying polymer electrolyte A having a negative charge to form a cured balloon-shaped closed pouch made of the coating film that is in intimate contact with the inner peripheral surface of the respiratory region; wherein polymer electrolyte A is selected from the group consisting of polyamino acids, artificially synthesized polypeptides, polysaccharides, hyaluronic acid, chondrotin, pectin, agarose, glycosaminoglycan, cellulose, starch, artificially synthesized polysaccharides, and mixtures thereof; and
shrinking the balloon-shaped closed pouch by reducing pressure inside the balloon-shaped closed pouch from outside of the respiratory region.

7. The method of claim 6, wherein the coating film-forming component is administered to the respiratory region in an amount of 0.004 g to 200 g per application.

8. The method of claim 6, wherein the coating film-forming component comprises a foaming agent.

9. The method of claim 6, wherein the balloon-shaped closed pouch is shrunk by:
removing residual gas in the respiratory region by suction; or
removing respiratory region volume reducer from the pulmonary alveoli or the alveolar sacs.

10. The method of claim 6, wherein the polymer electrolyte A is hyaluronic acid.

* * * * *